(12) United States Patent
Millar et al.

(10) Patent No.: US 11,701,485 B2
(45) Date of Patent: Jul. 18, 2023

(54) CATHETER MOUNT WITH SUCTION PORT

(71) Applicant: Fisher & Paykel Healthcare Limited, Auckland (NZ)

(72) Inventors: Gavin Walsh Millar, Auckland (NZ); Edwin Joseph Lyons, Auckland (NZ); Madeleine Bess Martin, Auckland (NZ); David Robert Kemps, Auckland (NZ)

(73) Assignee: Fisher & Paykel Healthcare Limited, Auckland (NZ)

( * ) Notice: Subject to any disclaimer, the term of this patent is extended or adjusted under 35 U.S.C. 154(b) by 368 days.

(21) Appl. No.: 17/126,665

(22) Filed: Dec. 18, 2020

(65) Prior Publication Data

US 2021/0170126 A1    Jun. 10, 2021

Related U.S. Application Data

(63) Continuation of application No. 16/532,875, filed on Aug. 6, 2019, now Pat. No. 10,898,667, which is a continuation of application No. 14/776,459, filed as application No. PCT/NZ2014/000037 on Mar. 14, 2014, now Pat. No. 10,413,687.

(60) Provisional application No. 61/785,798, filed on Mar. 14, 2013.

(51) Int. Cl.
| | |
|---|---|
| *A61M 16/00* | (2006.01) |
| *A61M 16/04* | (2006.01) |
| *A61M 16/08* | (2006.01) |
| *A61M 39/10* | (2006.01) |

(52) U.S. Cl.
CPC .... *A61M 16/0463* (2013.01); *A61M 16/0825* (2014.02); *A61M 16/0833* (2014.02); *A61M 39/1055* (2013.01); *A61M 16/0465* (2013.01)

(58) Field of Classification Search
CPC .......... A61M 16/0463; A61M 16/0825; A61M 16/0833; A61M 39/1055; A61M 16/0465
See application file for complete search history.

(56) References Cited

U.S. PATENT DOCUMENTS

| | | |
|---|---|---|
| 4,351,328 A | 9/1982 | Bodai |
| 4,475,548 A | 10/1984 | Muto |
| 4,531,328 A | 7/1985 | Jewett |

(Continued)

FOREIGN PATENT DOCUMENTS

| | | |
|---|---|---|
| AU | 2015264908 | 12/2015 |
| DE | 3538033 A1 | 4/1987 |

(Continued)

OTHER PUBLICATIONS

Extended European Search Report; dated Aug. 25, 2016; 8 pages.

(Continued)

*Primary Examiner* — Steven O Douglas
(74) *Attorney, Agent, or Firm* — Knobbe, Martens, Olson & Bear, LLP

(57) ABSTRACT

A catheter mount is configured to be attached to a respiratory apparatus. The catheter mount includes a plurality of ports in fluid communication with each other. The plurality of ports include an interface port configured to connect to an interface tube, a conduit port configured to connect to a conduit tube, and at least one suction port configured to allow insertion of a suction catheter. The at least one suction port can be positioned to allow the suction catheter, when inserted, access to both the interface port and conduit port.

20 Claims, 31 Drawing Sheets

(56) References Cited

U.S. PATENT DOCUMENTS

| | | |
|---|---|---|
| D282,772 S | 2/1986 | Fleury |
| 4,569,344 A | 2/1986 | Palmer |
| 4,836,199 A | 6/1989 | Palmer |
| 5,060,646 A | 10/1991 | Page |
| 5,135,489 A | 8/1992 | Jepson et al. |
| 5,255,676 A | 10/1993 | Russo |
| 5,259,376 A | 11/1993 | Bales |
| 5,309,902 A | 5/1994 | Kee et al. |
| 5,329,921 A | 7/1994 | Socaris et al. |
| 5,333,606 A | 8/1994 | Schneider et al. |
| 5,343,857 A | 9/1994 | Schneider et al. |
| 5,501,214 A | 3/1996 | Sabo |
| 5,513,628 A | 5/1996 | Coles et al. |
| 5,549,554 A | 8/1996 | Miraki |
| 5,598,840 A | 2/1997 | Iund et al. |
| 5,640,951 A | 6/1997 | Huddart et al. |
| 5,694,922 A | 12/1997 | Palmer |
| 5,711,294 A | 1/1998 | Kee et al. |
| 5,715,815 A | 2/1998 | Lorenzen et al. |
| 5,775,325 A | 7/1998 | Russo |
| 5,779,687 A | 7/1998 | Bell et al. |
| 6,086,529 A | 7/2000 | Arndt |
| 6,217,568 B1 | 4/2001 | Jepson et al. |
| 6,245,048 B1 | 6/2001 | Fangrow, Jr. et al. |
| 6,261,266 B1 | 7/2001 | Jepson et al. |
| 6,269,813 B1 | 8/2001 | Fitzgerald et al. |
| 6,287,280 B1 | 9/2001 | Lampropoulos et al. |
| D453,221 S | 1/2002 | Haytman et al. |
| 6,575,944 B1 | 6/2003 | McNary et al. |
| 6,615,835 B1 | 9/2003 | Cise et al. |
| 6,702,789 B1 | 3/2004 | Owens et al. |
| 6,758,833 B2 | 7/2004 | Lopez |
| 6,769,430 B1 | 8/2004 | Carlsen et al. |
| 6,923,184 B1 | 8/2005 | Russo |
| 6,935,339 B2 | 8/2005 | Mattar Neto et al. |
| 6,978,783 B2 | 12/2005 | Svendsen |
| 7,523,967 B2 | 4/2009 | Steppe |
| 7,549,419 B2 | 6/2009 | Carlsen et al. |
| 7,665,465 B2 | 2/2010 | Radney |
| 7,803,139 B2 | 9/2010 | Fangrow, Jr. |
| 8,105,314 B2 | 1/2012 | Fangrow, Jr. |
| 8,679,090 B2 | 3/2014 | Anderson et al. |
| 9,022,036 B2 | 5/2015 | Graham et al. |
| 9,517,321 B2 | 12/2016 | Buechi et al. |
| 9,878,120 B2 | 1/2018 | White et al. |
| 9,993,608 B2 | 6/2018 | Cheung et al. |
| 10,413,687 B2 | 9/2019 | Millar et al. |
| 10,456,543 B2 | 10/2019 | Graham et al. |
| 11,027,084 B2 | 6/2021 | Graham et al. |
| 2001/0044600 A1 | 11/2001 | Elkins |
| 2002/0078960 A1 | 6/2002 | Cise |
| 2002/0087144 A1 | 7/2002 | Zinger et al. |
| 2003/0106559 A1 | 6/2003 | Svendsen |
| 2004/0007236 A1 | 1/2004 | McGee |
| 2004/0181192 A1 | 9/2004 | Cuppy |
| 2004/0255952 A1 | 12/2004 | Carlsen et al. |
| 2006/0025724 A1 | 2/2006 | Chen |
| 2006/0064065 A1 | 3/2006 | Russo |
| 2006/0149189 A1 | 7/2006 | Diamond et al. |
| 2006/0212000 A1 | 9/2006 | Fangrow, Jr. |
| 2006/0249153 A1 | 11/2006 | DeVries et al. |
| 2006/0249160 A1 | 11/2006 | Scarberry et al. |
| 2006/0283447 A1 | 12/2006 | Dhuper et al. |
| 2008/0271741 A1 | 11/2008 | Graham et al. |
| 2008/0287906 A1 | 11/2008 | Burkholz et al. |
| 2009/0182309 A1 | 7/2009 | Muffly |
| 2010/0154797 A1 | 6/2010 | Landis et al. |
| 2010/0163051 A1 | 7/2010 | Brewer et al. |
| 2011/0067699 A1 | 3/2011 | Caruso et al. |
| 2013/0269686 A1 | 10/2013 | Pezzano et al. |
| 2014/0311487 A1 | 10/2014 | Buechi et al. |
| 2015/0314093 A1 | 11/2015 | Chiu |
| 2016/0038700 A1 | 2/2016 | White et al. |
| 2018/0078728 A1 | 3/2018 | Holyoake et al. |
| 2019/0224439 A1 | 7/2019 | Lopez Muedano et al. |
| 2019/0321579 A1 | 10/2019 | Hermez et al. |

FOREIGN PATENT DOCUMENTS

| | | |
|---|---|---|
| DE | 202006007397 | 9/2007 |
| DE | 102007003454 | 7/2008 |
| EP | 1729842 | 12/2006 |
| EP | 2628498 | 8/2013 |
| EP | 2928533 | 10/2015 |
| WO | WO 93/021981 | 11/1993 |
| WO | WO 96/09082 A1 | 3/1996 |
| WO | WO 96/26757 | 9/1996 |
| WO | WO 99/29359 | 6/1999 |
| WO | WO 01/021241 | 3/2001 |
| WO | WO 02/28463 | 4/2002 |
| WO | WO 2005/048982 | 6/2005 |
| WO | WO 2005/094925 | 10/2005 |
| WO | WO 2008/023147 | 2/2008 |
| WO | WO 2008/142359 | 11/2008 |
| WO | WO 2009/136871 | 11/2009 |
| WO | WO 2015/060731 | 4/2015 |
| WO | WO 2018/070883 | 4/2018 |
| WO | WO 2018/217105 | 11/2018 |

OTHER PUBLICATIONS

International Search Report, dated Jun. 8, 2005.
International Search report; PCT/NZ2014/000037; dated May 2, 2014; 3 pages.
International Search Report; PCT/NZ2018/050088; dated Sep. 17, 2018; 6 pages.
Written Opinion; PCT/NZ2018/050088; dated Sep. 17, 2018; 9 pages.
Extended European Search Report; dated Dec. 16, 2019; 5 pages.
Supplemental European Search Report; EP 05728181.8; dated May 3, 2017; 3 pages.
Extended European Search Report for European Patent Application No. 20173285.6, dated Dec. 10, 2020 in 8 pages.

CATHETER MOUNT WITH SUCTION PORT

INCORPORATION BY REFERENCE TO ANY PRIORITY APPLICATIONS

Any and all applications for which a foreign or domestic priority claim is identified in the Application Data Sheet as filed with the present application are hereby incorporated by reference under 37 CFR 1.57.

BACKGROUND OF THE INVENTION

Field of the Invention

The present invention generally relates to respiratory devices having assemblies for handling liquids and particulate matter. More particularly, the present invention relates to assemblies that facilitate suctioning materials from within the respiratory gas flow conduits.

Description of the Related Art

There are a number of medical procedures that require placement of a tracheostomy or endotracheal tube into the windpipe of a patient to deliver air directly into the lungs. For example, such patients may be connected to a ventilator to assist with breathing.

Over time, condensation, secretions, particulate matter and the like may accumulate within the system. A catheter mount can be positioned between the ventilator and the patient interface. The catheter mount allows access to the patient interface using a suction catheter. Unfortunately, however, catheter mounts are not currently configured to provide easy access to the components between the catheter mount and the ventilators.

SUMMARY OF THE INVENTION

Accordingly, certain features, aspects and advantages of the present invention relate to a catheter mount configured to facilitate easy access for a suction catheter to portions of the system upstream and downstream of the catheter mount. As such, certain features, aspects and advantages of the present invention facilitate suctioning of secretions and condensate from the intermediate tube using standard suction catheters. In some configurations, the catheter mount features a head geometry that is designed to have one or more access points that facilitate insertion of the catheter tube along the endotracheal tube axis and the intermediate tube axis. In some configurations, the head geometry comprises a dual valve feature and in some configurations the head geometry comprises a single valve angled to provide access to both axes. In some configurations, the valve extends in a plane that is at other than about 90 degrees and 180 degrees relative to one or more of the axes. In some configurations, the axes may be at other than about 90 degrees relative to each other and the valve may extend in a plane that is at about 90 degrees relative to one of the axes. In some configurations, two valves are used, the two axes are at about 90 degrees relative to each other and the two valves extend in planes that are at about 90 degrees relative to each other. In some configurations, one valve is in a plane that is about 90 degrees relative to one of the axes but the two axes are adjustable relative to each other. In some configurations, a diverting feature can be movable into an air passage to divert the catheter from a first direction toward a second direction.

A catheter mount arranged and configured in accordance with certain features, aspects and advantages of the present invention can be configured to be attached to a respiratory apparatus. The catheter mount can comprise a plurality of ports in fluid communication with each other. The plurality of ports can comprise an interface port configured to connect to an interface tube, a conduit port configured to connect to a conduit tube and at least one suction port configured to allow insertion of a suction catheter. In some configurations, the at least one suction port is positioned to allow the suction catheter, when inserted, access to both the interface port and conduit port.

In some configurations, the angle between the interface axis and the conduit axis is less than 90 degrees and the at least one suction port is substantially centered axially with either the interface port or the conduit port.

In some configurations, the angle between the interface axis and the conduit axis is approximately 75 degrees.

In some configurations, the at least one suction port is at an intermediate angle with respect to the interface port and the conduit port.

In some configurations, the intermediate angle is approximately 45 degrees with respect to the interface port and the conduit port.

In some configurations, the at least one suction port is larger than either the interface port or the conduit port.

In some configurations, the at least one suction port is at least about 1.2 times larger than either the interface port or the conduit port.

In some configurations, the catheter mount also comprises a switch with the at least one suction port being substantially centered axially with either the interface port or the conduit port and the switch having a first position configured to not interfere with the trajectory of the suction catheter inserted into the at least one suction port and a second position configured to alter the trajectory of a suction catheter inserted into the at least one suction port.

In some configurations, the switch comprises a button located on the exterior of the catheter mount.

In some configurations, a first suction port of the at least one suction port is substantially centered axially with the interface port and wherein a second suction port of the at least one suction port is substantially centered axially with the conduit port.

In some configurations, at least one of the conduit port or the interface port are attached to a rotatable assembly.

In some configurations, the rotatable assembly is a ball-joint assembly.

In a further aspect the invention consists in components as herein described with reference to any one or more of the drawings.

The term "comprising" as used in this specification and claims means "consisting at least in part of". When interpreting each statement in this specification and claims that includes the term "comprising", features other than that or those prefaced by the term may also be present. Related terms such as "comprise" and "comprises" are to be interpreted in the same manner.

This invention may also be said broadly to consist in the parts, elements and features referred to or indicated in the specification of the application and/or statements of invention, individually or collectively, and any or all combinations of any two or more said parts, elements features or statements of invention, and where specific integers mentioned herein which have known equivalents in the art to which this invention relates, such known equivalents are deemed to be incorporated herein as if individually set forth.

The invention consists in the foregoing and also envisages constructions of which the following gives examples only.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

Further aspects and advantages of the present invention will become apparent from the ensuing description which is given by way of example only.

DETAILED DESCRIPTION OF THE PREFERRED EMBODIMENT

Figure 1A:
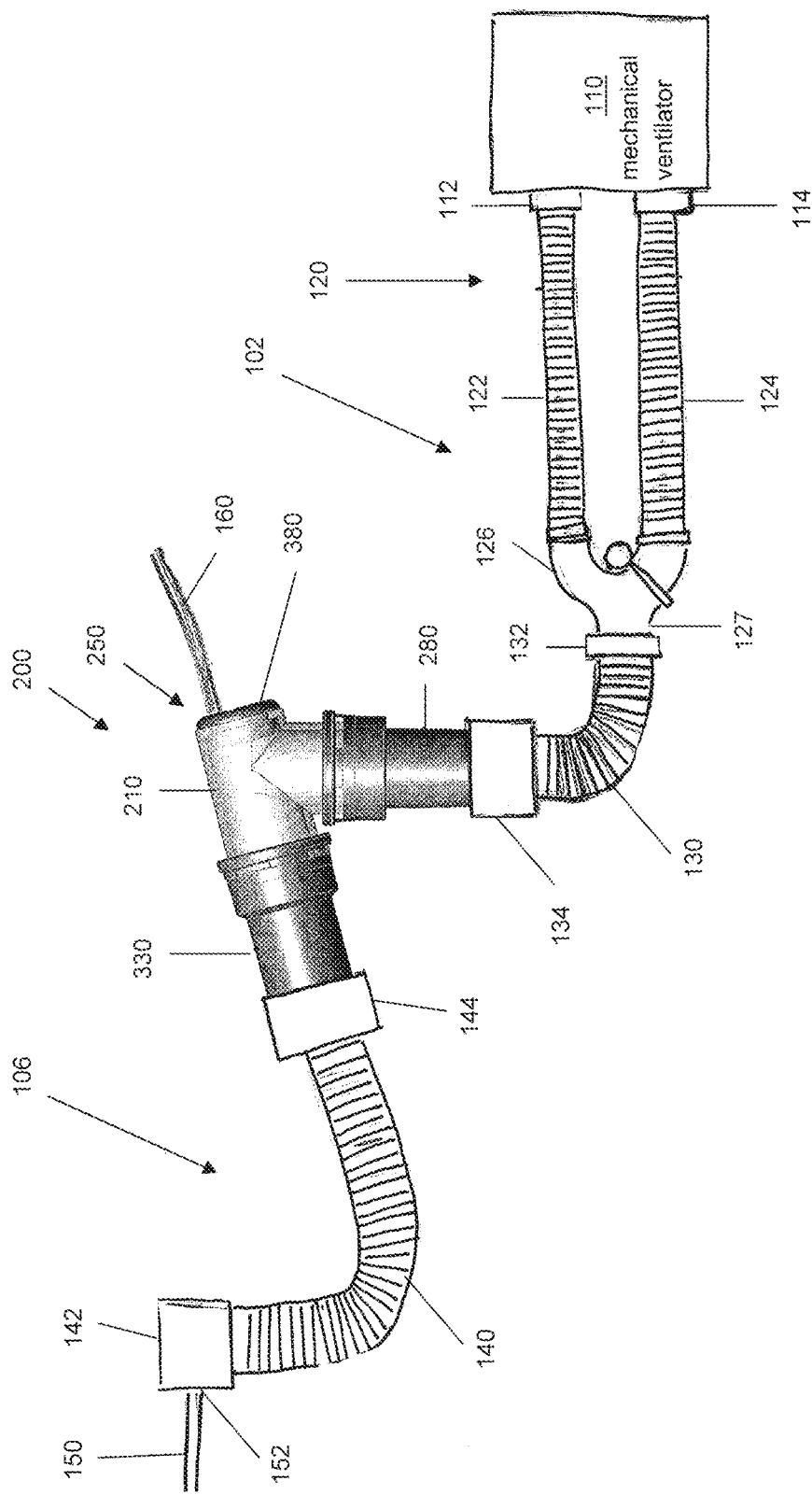
FIG. 1A is an illustration of a respiratory assistance system that includes an embodiment of a catheter mount that is arranged and configured in accordance with certain features aspects and advantages of the present invention.
Figure 1B:
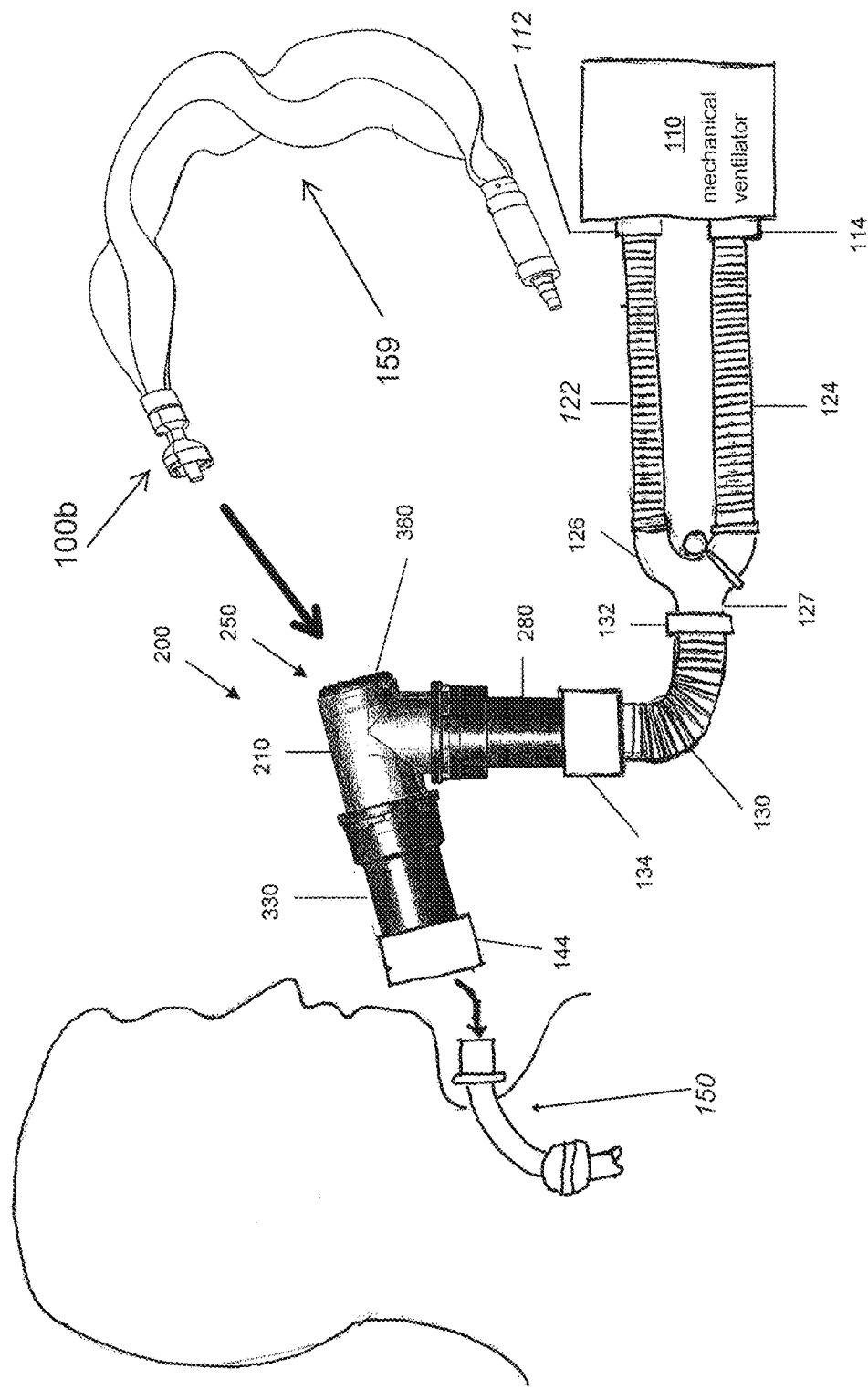
FIG. 1B is an illustration of the respiratory system of FIG. 1A with a different connection to a patient interface and a closed bag-type suction system.
Figure 1C:
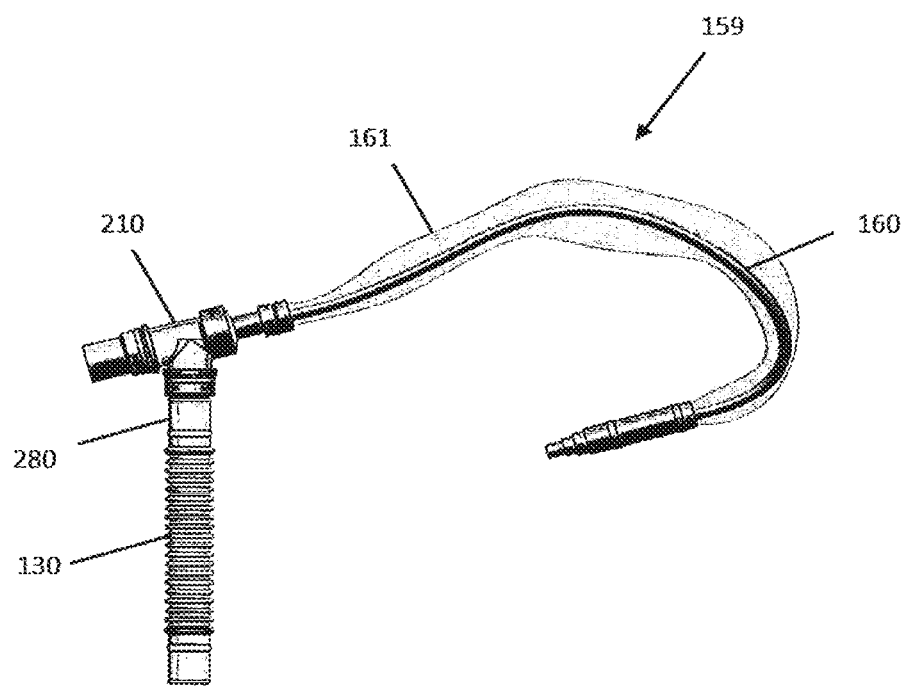
FIG. 1C is an illustration of part of a system similar to that shown in FIG. 1B including a closed bag-type suction system.

FIG. 1A shows a simple, closed-loop respiratory assistance system 100a. The system 100a can include a catheter mount 200, a mechanical ventilator 110 and an interface 150. For purposes of this description, all tubing between the mechanical ventilator 110 and the catheter mount 200 will be termed conduit tubing 102 and all tubing between the catheter mount 200 and the interface 150 will be termed interface tubing 106. The mechanical ventilator 110 can include an inspiratory port 112 that supplies a flow to the interface 150 and an expiratory port 114 that receives a flow from the interface 150. FIG. 1B shows a system 100b similar to FIG. 1A with a different connection to the patient and a different suction system 159 (i.e., a closed bag-type suction system) relative to FIG. 1A that connects to catheter suction port 250. FIG. 1C shows part of a system similar to FIG. 1B with a closed bag-type suction system 159, including a suction catheter 160 provided in a flexible sheath 161, attached to the catheter mount 200.

In the embodiment shown in FIGS. 1A and 1B, the mechanical ventilator 110 assists a user by cycling through periods of relatively high positive pressure (i.e., pressures above ambient pressure) during inhalation and periods of relatively low pressure during exhalation. The inspiratory port 112 can be connected to the inspiratory tube 122 of a breathing circuit assembly 120 and the expiratory port 114 can be connected to the expiratory tube 124 of the breathing circuit assembly 120. The inspiratory tube 122 and the expiratory tube 124 may be cylindrical in shape and therefore have a generally circular cross-section; however, other tube cross-sectional shapes, such as ellipses, ovals, or polygons may be also be used, for example but without limitation. The tubes 122, 124 can be manufactured from any type of material, such as, but not limited to, plastics, metals, composites, or other polymers. Additionally, in some embodiments, the tubes 122, 124 may be corrugated, as shown in FIGS. 1A and 1B, to further improve the flexibility of the tubes. In other embodiments, at least a portion of at least the inner bores of the tubes can be smooth to inhibit the collection of condensates, secretions, and other materials in the tubes.

At the opposite end of the breathing circuit assembly 120 is a connector 126, such as a 'Y' or 'T' connector. The connector 126 can merge the inspiratory tube 122 and the expiratory tube 124 with a single collector port 127. The collector port 127 enables the use of a single tube downstream of the connector 126. The single tube can connect the connector 126 to the interface 150. Thus, both inhalation gases and exhalation gases may pass through the single tube during a patient's breathing cycle. The connector 126 may be made of the same materials as those used for the inspiratory and expiratory tubes 122, 124 or may be made of different materials. As shown, unlike the inspiratory and expiratory tubes 122, 124, the connector 126 may be formed without corrugation such that the connector 126 exhibits a greater degree of rigidity and resistance to flexing. In other embodiments, one or more portion of the connector 126 may include corrugations.

With continued reference to the embodiment of the system 100a shown in FIG. 1A, a catheter mount 200 couples the conduit tube 130 with an interface tube 140. The illustrated catheter mount 200 includes a mount body 210, a conduit tube reverse connector 280, an interface tube reverse connector 330, and a valve 380 that is configured to allow insertion of a suction catheter 160 for removal of any condensates, particulates or other matter located in either the conduit or the interface tubes 130, 140, for example but without limitation. In some configurations, as shown in FIG. 1B, the catheter 160 can be part of a closed bag-type suction system where the catheter 160 is surrounded by and moveable within a bag or other enclosure that is permanently or semi-permanently coupled to the catheter mount proximate the valve 380, as shown in FIG. 1C. The arrangement shown in FIG. 1C may be connected to an interface 150 and a breathing circuit assembly 120 in a similar manner to that shown in FIGS. 1A and 1B.

The conduit tube 130, such as an intermediate tube as shown in FIG. 1A, may couple the breathing circuit assembly 120 and the catheter mount 200. The conduit tube 130 can be attached to the connector 126 at the collector exit port 127 via a collector connector 132 and can be connected to the catheter mount 200 at the reverse conduit tube connector 280 using the mount connector 134. In the embodiment of system 100 illustrated in FIG. 1A, the two connectors 134, 280 are directly attached to each other with an interference fit, a press fit, or a friction fit due to the elasticity of the materials used for the two components 134, 280. However, other types of coupling mechanisms, such as a snap fit, a bayonet socket, threads, screws, tightening collars, retention collars, or other similar mechanisms may be used to secure the two components 134, 280 to each other. In some embodiments, the construction of the conduit tube 130 is similar to that of the construction of the inspiratory and/or expiratory tubes 122, 124. However, in other embodiments, the construction may differ depending on operational requirements or desired operating characteristics of the conduit tube 130, such as an intermediate tube as shown in FIG. 1A. For example, the conduit tube 130 may be made of a smooth, rather than corrugated, material to inhibit the collection of condensates, secretions, and other materials in the conduit tube 130.

The interface tube 140 couples the interface mechanism 150, such as the endotracheal tube as illustrated in FIG. 1A, with the catheter mount 200. As shown in FIG. 1B, in some configurations, the catheter mount 200 can directly connect to the interface mechanism 150, such as the endotracheal tube as illustrated in FIG. 1B, without the interface tube 140 shown in FIG. 1A. As with the intermediate tube 130, the interface tube 140 is attached to the catheter mount 200 at the reverse interface tube connector 330 via the mount connector 144 and attached to the interface 150 at interface inlet 152 via an interface connector 142. Similar to the conduit tube 130, in the embodiment of system 100a illustrated in FIG. 1A, the two connectors 144, 330 can be directly attached to each other with an interference fit, a press fit, or a friction fit due to the elasticity of the materials used for the two components 144, 330. However, other types of coupling mechanisms, such as a snap fit, a bayonet socket, threads, screws, tightening collars, retention collars, or other similar mechanisms may also be used. In some embodiments, the construction of the interface tube 140 is similar to that of the construction of the inspiratory and/or expiratory tubes 122, 124 or the conduit tube 130. However, in other embodiments, the construction may differ depending on operational requirements or desired operating characteristics of the interface tube 130. For example, the interface tube 140 may be made of a smooth, rather than corrugated, material to inhibit the collection of condensates, secretions, and other materials in the interface tube 140.

The catheter mount 200 need not be limited to uses with the closed-loop respiratory assistance system 100a as shown in FIG. 1A. In addition, the placement of the catheter mount 200 need not be limited to coupling the interface tube 140 with the conduit tube 130. Rather, the catheter mount 200 can be used in any type of system that couples two tubes and/or a tube to an interface. Furthermore, for breathing circuits, other devices may also be included and placed anywhere in the system such as, but not limited to, humidifiers, vaporizers, filters, valves, CO2 sensors and the like. In addition, some system components shown in FIGS. 1A-1C or described above may be omitted in alternative embodiments. For example, in some embodiments, the mechanical ventilator 110 may be omitted or replaced with another component. In addition, other interfaces 150, such as nasal cannulas, vented or non-vented face masks, and tracheostomy tubes can be used, for example but without limitation.

Angled Catheter Mount

FIGS. 2-5 are illustrations of an embodiment of an angled catheter mount 200a. The angled catheter mount 200a comprises a conduit port 250a and an interface port 300a that are oriented at such an angle as to allow a suction catheter 160 access to both connectors and the corresponding tubes attached thereto. As illustrated in FIGS. 2A-2D, this embodiment of the angled catheter mount 200a also has a suction port 350a positioned generally opposite the interface port 300a. In other embodiments, the suction port 350a can be oriented opposite the conduit port 250a. The angled catheter mount 200a has a mount body 210a configured to allow fluid communication between the conduit port 250a and the interface port 300a through an interior flow channel 212a (see FIGS. 2B-2D). The suction port 350a allows selective access to the interior flow channel 212a.

The conduit port 250a can be configured to receive a conduit tube 130 from a respiratory assistance system as described above. In some embodiments, the conduit tube 130 is an intermediate tube that serves as an intermediary connector between the angled catheter mount 200a and the remaining conduit tubing 102. In some embodiments, the conduit port 250a of the angled catheter mount 200a can receive a conduit tube reverse connector 280a configured to receive a conduit tube 130, such as an intermediate tube, from the system 100a, 100b. The reverse connector 280a can be attached to the angled catheter mount 200a to facilitate connecting the angled catheter mount 200a with a conduit tube 130 and to potentially create a more advantageous seal between the attached conduit tubing 102 and the catheter mount 200a. As will be discussed in greater detail below, the conduit tube reverse connector 280a may be made of a material different from that of the mount body 210a, which could provide greater elasticity and therefore form a better seal around both the mount body 210a and the conduit tube 130.

In alternative embodiments, the conduit tube 130 is attached directly to the mount body 210a. In one such embodiment, the conduit tube 130 is attached to the mount body 210a via an interference fit, a press fit, or a friction fit, for example, caused by the elasticity of the materials used for either or both of the two components 130, 210a. However, other types of coupling mechanisms, such as a snap fit, a bayonet socket, threads, screws, tightening collars, retention collars, or other similar mechanisms could also be used for attachment. In some embodiments, the conduit tube 130 may have a female mount connector 134, which is illustrated in FIG. 1A. In some embodiments, the conduit tube 130 may have a male mount connector that can be inserted into the channel 260a (see FIG. 3B).

The interface port 300a can be configured to receive an interface tube 140 from the respiratory assistance system 100a, 100b, for example. In some embodiments, the interface tube 140 can be attached to an interface 150, such as an endotracheal tube. In some embodiments, the interface tube 140 may be attached to nasal cannulas, vented or non-vented face masks, tracheostomy tubes and the like. As with the conduit port 250a, in some embodiments, an interface tube reverse connector 330a can be attached at the interface port 300a of the angled catheter mount 200a, which is configured to receive an interface tube 140 of the system 100a, 100b, for example. The reverse interface connector 330a can facilitate connecting the angled catheter mount 200a to an interface tube 140 and may also create a better seal between the catheter mount 200a and the interface tube 140. The interface tube reverse connector 330a can be similar in construction to the conduit tube reverse connector 280a. In some embodiments, the interface tube reverse connector 330a is of the same dimensions and materials as the conduit tube reverse connector 280a. In other embodiments, the interface tube reverse connector 330a has different dimensions and/or materials.

In some embodiments, the optional interface tube reverse connector 330a is not used and the interface tube 140 is directly attached to the catheter mount body 210a. In one such embodiment, the interface tube 140 can be attached to the mount body 210a via an interference fit, a press fit, or a friction fit caused by the elasticity of the materials used for either or both of the two components 140, 210a. However, other types of coupling mechanisms, such as a snap fit, a bayonet socket, threads, screws, tightening collars, retention collar, or other similar mechanisms known in the art also could be used. In some embodiments, the interface tube 140 may have a female mount connector 144, such as that illustrated in FIG. 1A. In some embodiments, the interface tube 140 may have a male mount connector that can be inserted into the channel 310a (see FIG. 3B). While it is preferable that the coupling mechanism for both the conduit port 250a and the interface port 300a be the same, some embodiments can include ports 250a, 300a that have different coupling mechanisms.

The suction port 350a can be configured to selectively receive a suction catheter 160. The catheter 160 can be used, when necessary or desired, to suction condensate, secretions, and other matter from within the passages defined by one or more of the mount body 210a, the conduit port 250a and any attached tubing thereto such as the conduit tube 130, and the interface port 300a and any attached tubing thereto such as the interface tube 140. Removal of condensate, secretions, and other such matter from the tubes of the respiratory assistance system can be desired for many reasons. The suction section can include a valve 380a that generally seals the angled catheter mount 210a and reduces the likelihood of fluid flowing into or out of the suction port 350a when a suction catheter 160 is not being used. The valve 380a will be discussed in greater detail below.

Angled Catheter Mount

Figure 2A:
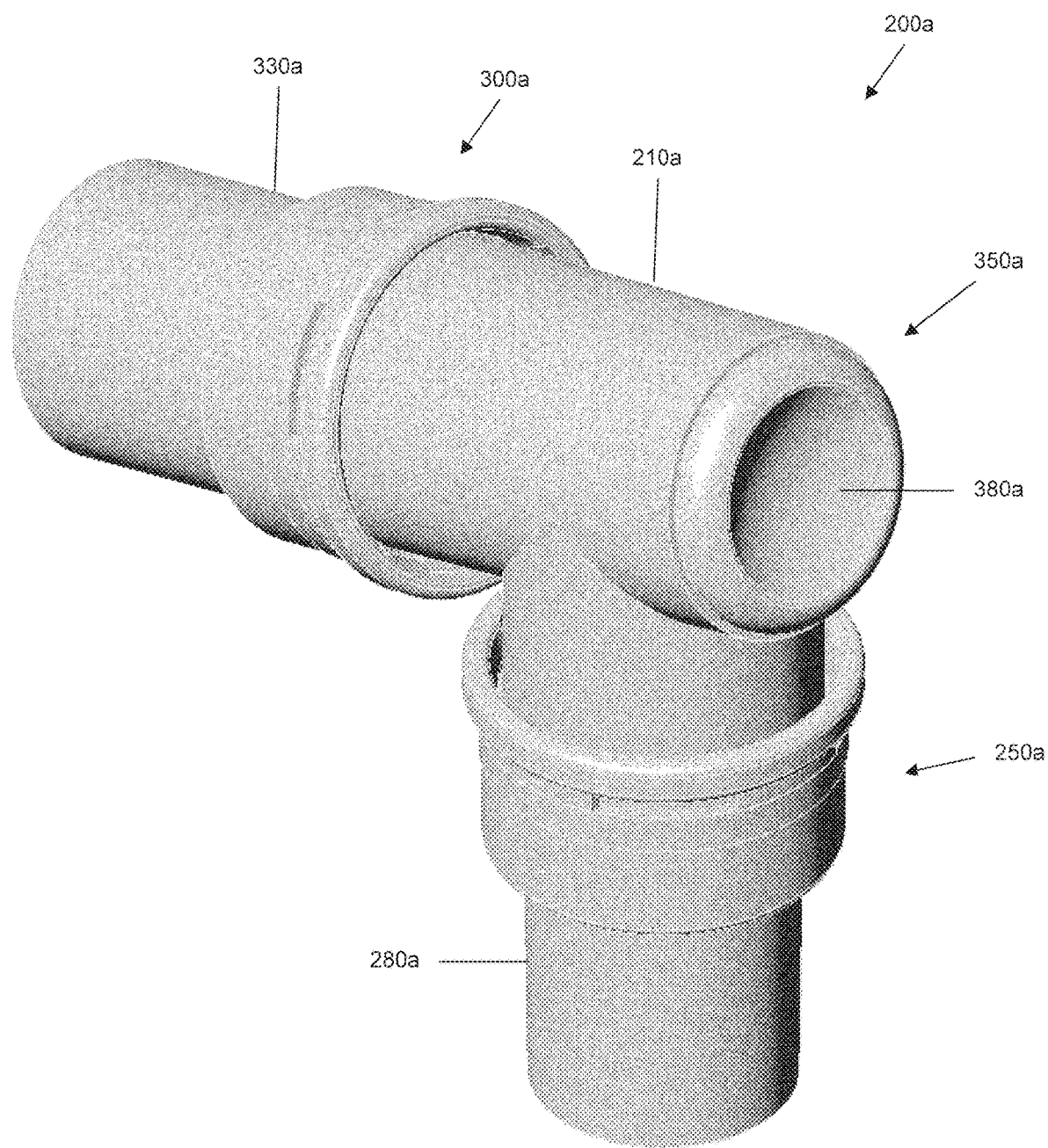
FIG. 2A is a perspective view of an embodiment of a catheter mount that is arranged and configured in accordance with certain features, aspects and advantages of the present invention.
Figure 2B:
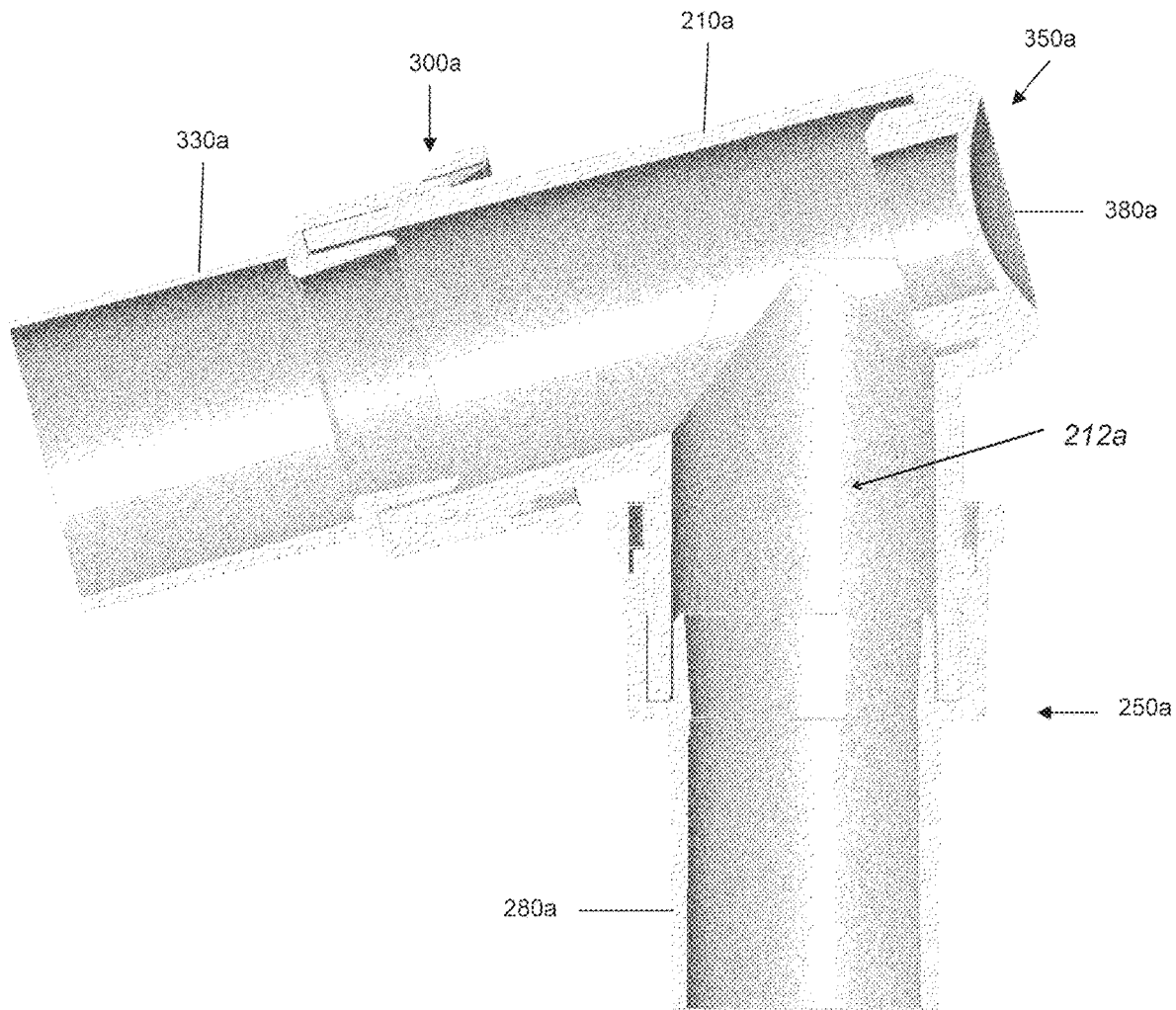
FIG. 2B is a section view of the catheter mount of FIG. 2A.
Figure 2C:
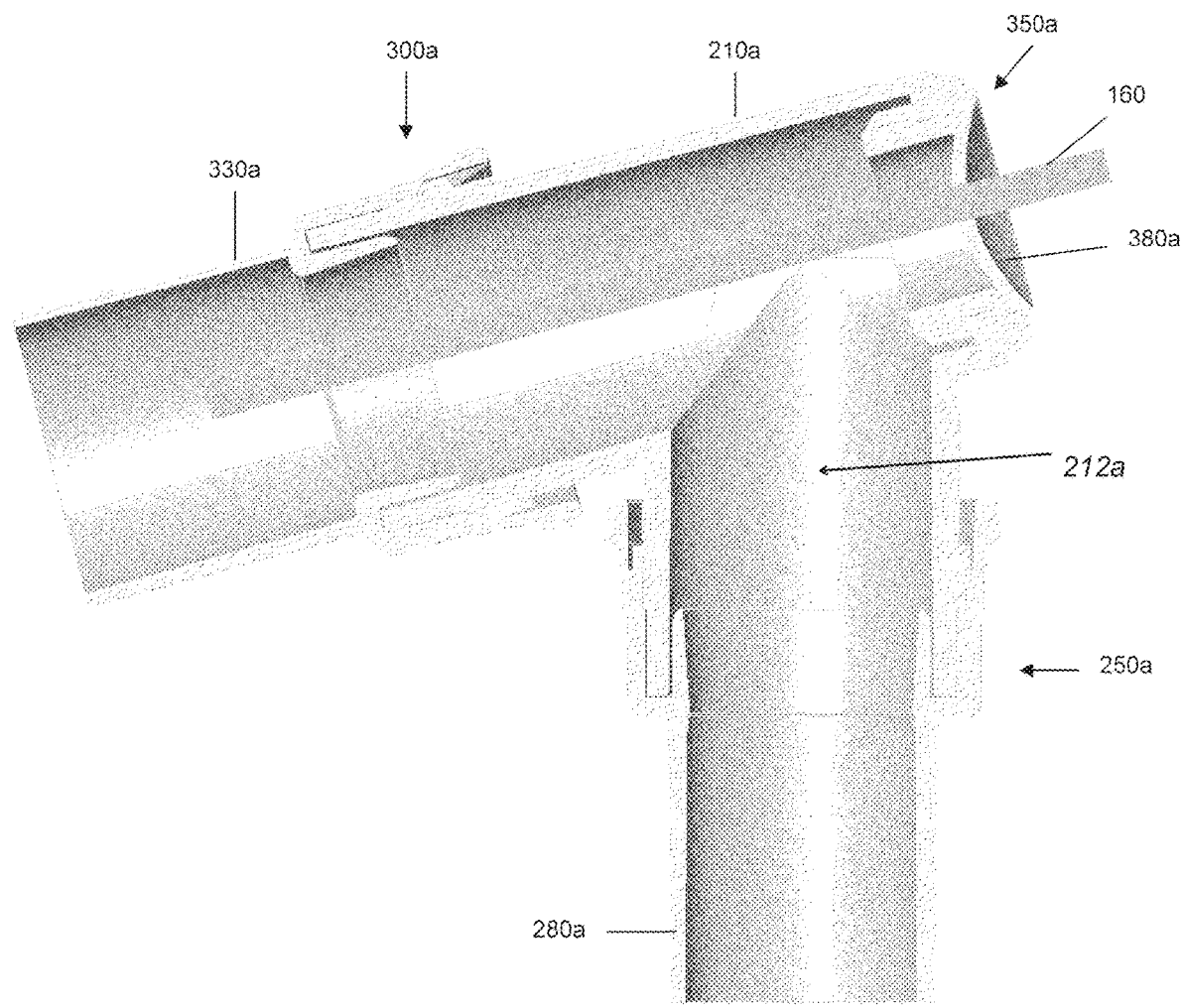
FIG. 2C is a section view of the catheter mount of FIG. 2A showing a schematic suction tube inserted into a first portion of the catheter mount.
Figure 2D:
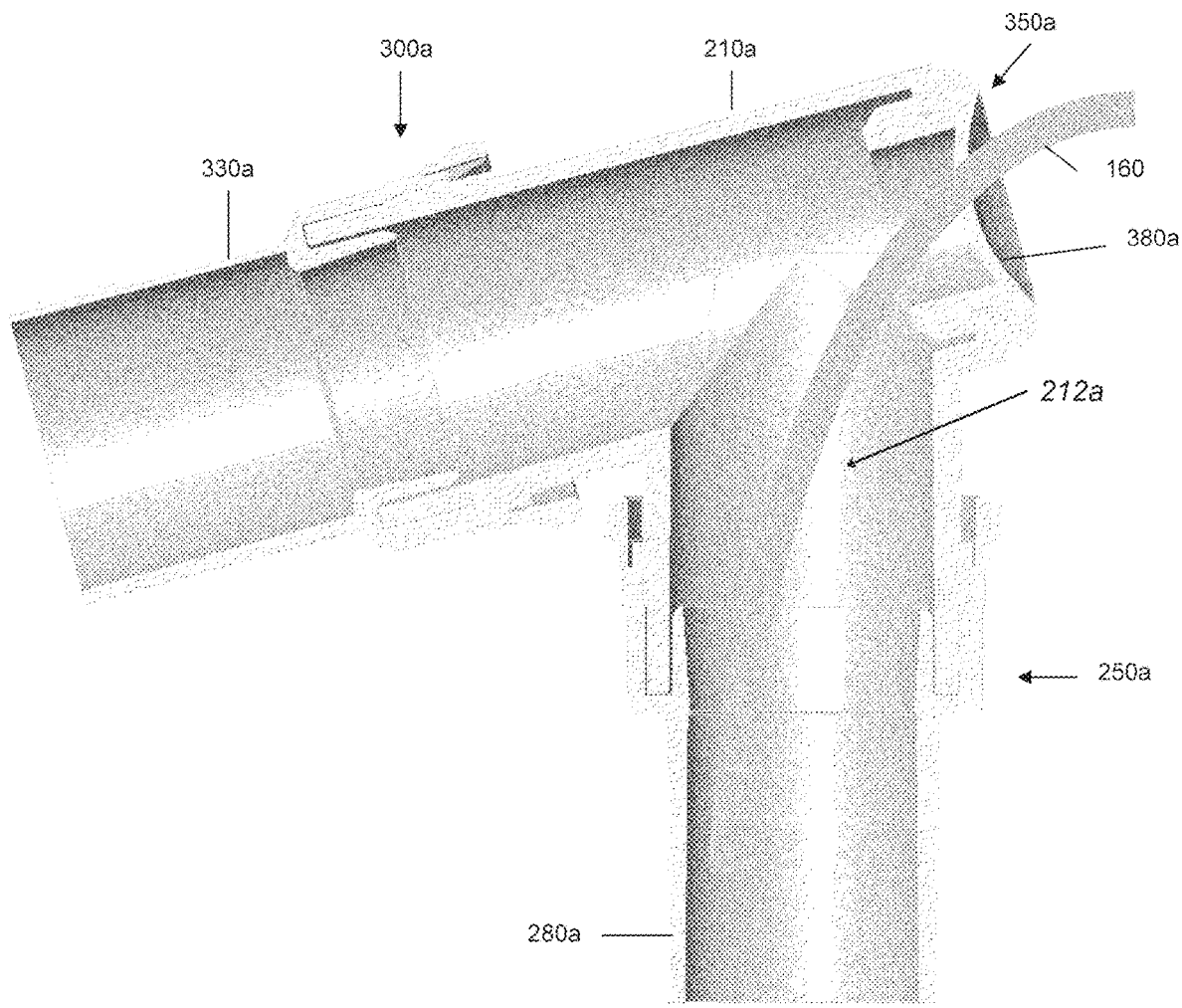
FIG. 2D is a section view of the catheter mount of FIG. 2A showing a schematic suction tube inserted into a second portion of the catheter mount.
Figure 3A:
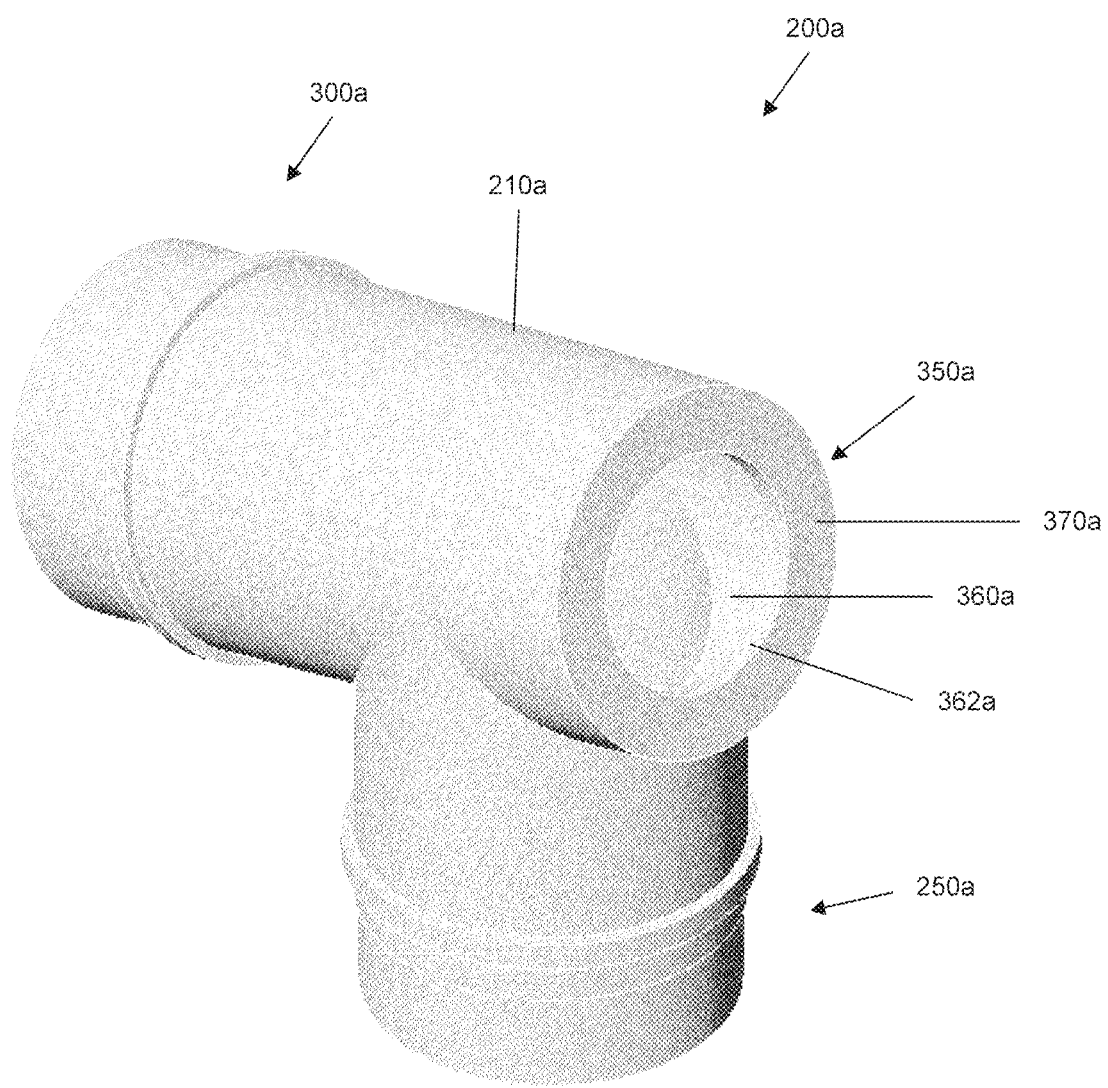
FIG. 3A is a perspective view of an embodiment of a catheter mount that is arranged and configured in accordance with certain features, aspects and advantages of the present invention.
Figure 3B:
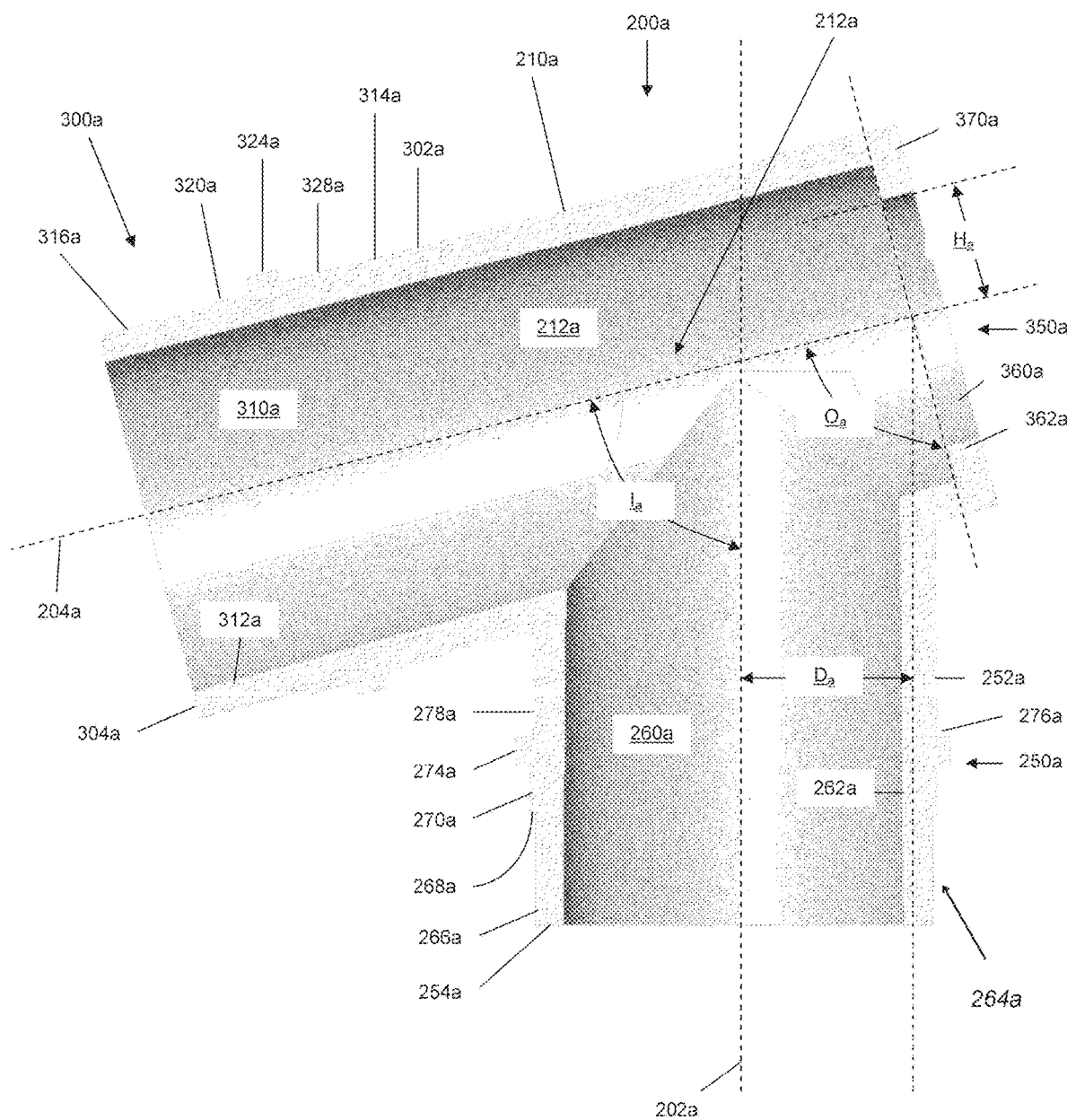
FIG. 3B is a side section view of the catheter mount of FIG. 3A.

FIGS. 3A and 3B are illustrations of the angled catheter mount 200a of FIGS. 2A-2D showing the mount body 210a without the conduit tube reverse connector 280a, the interface tube reverse connector 330a, and the valve 380a. The connectors can be swivel-type connectors that engage about, or that receive, the catheter mount ports. Traditionally, the catheter mount receives the connectors. By having the connectors receive the ports, it is easier to connect and disconnect tubing and the interface from the catheter mount.

As shown most clearly in FIG. 3B, the mount body 210a can be hollow and can be configured to allow fluid communication between the conduit port 250a and the interface port 300a. The suction port 350a can allow selective access to the flow channel 212a. The flow channel 212a generally can be defined by the channel 260a of the conduit port 250a and the channel 310a of the interface port 300a.

With continued reference to FIG. 3B, the conduit port 250a of the mount body 210a can include a generally cylindrical tubular member 252a that is rotated about the conduit axis 202a. The channel 260a can be centered along the conduit axis 202a and can extend along the length of the tubular member 252a. The channel 260a of the conduit port 250a can define the inner surface 262a of the tubular member 252a. The channel 260a can have a circular cross-sectional shape that generally tapers with a decreasing radial dimension about the conduit axis 202a when moving from the end 254a of the tubular member 252a toward the suction port 350a. The tapering enables tubes inserted into the channel 260a to be subject to a decreased radial dimension with further insertion. Such a decrease in radial dimension can provide a better seal.

In some embodiments, this radial dimension of the channel 260a remains constant throughout the length of the channel 260a. In some embodiments, this radial dimension of the passage 260a increases when moving from the end 254a to the suction port 350a. The radial dimension of the channel 260a and the degree of tapering, if any, of the channel 260a can be dependent upon the desired flow characteristics through the flow channel 212a of the mount body 210a as well as considerations regarding sealing for tubes inserted into the channel 260a. Furthermore, other embodiments of the mount body 210a have channels 260a of different cross-sectional shapes such as, but not limited to, ovals, ellipses, or polygons. In yet other embodiments, the channel 260a is offset from the conduit axis 202a.

In some embodiments, the inner surface 262a of the tubular member 252a can be relatively smooth with no protrusions or other abrupt changes in diameter. A presence of protrusions or other abrupt changes in diameter can potentially accelerate the accumulation of condensates, secretions, and other matters by obstructing flow and by providing a surface upon which such condensate, secretions, and other matter can collect. In some embodiments, such protrusions along the inner surface 262a may exist for other beneficial purposes such as, but not limited to, coupling mechanisms for either the conduit tube reverse connector 280a or the conduit tube 130. For example, in embodiments where the conduit tube 130 is directly attached to the tubular member 252a of the mount body 210a, the mount end of the conduit tube 130 may be a male connector that is inserted into the channel 260a. Under such circumstances, it could potentially be beneficial to include an annular protrusion on the inner surface 262a to provide a better seal and to reduce the likelihood of the accumulation of condensate, secretions, and material on the tip of the conduit tube 130. Such an annular protrusion can also be used with the conduit tube reverse connector 280a, which has an inner tubular member 424 that is inserted into the channel 260a.

In contrast, in some embodiments of the angled catheter mount 200a, the outer surface of the tubular member 252a can have multiple protrusions that are configured to attach to the conduit tube reverse connector 280a or that are configured to attach to the mount connector 134 of the conduit tube 130. Moving from the end 254a of the tubular member 252a to the suction port 350a, the outer surface 264a of this embodiment has an annular slot 266a, an intermediate annular protrusion 270a, an annular locking protrusion 274a, and an annular depression 278a. The annular slot 266a has a first radial dimension about the conduit axis 202a. The intermediate annular protrusion 270a has a second radial dimension about the conduit axis 202a. The annular locking protrusion 274a a third radial dimension about the conduit axis 202a. Lastly, the annular depression 278a has a fourth radial dimension about the conduit axis 202a.

In the embodiment as illustrated in FIG. 3B, the first radial dimension is less than the second and third radial dimensions. The fourth radial dimension is less than the third radial dimension and approximately equal to the second radial dimension. Preferably, the fourth radial dimension is chosen such that locking ramps 452 of the interlock section 450 (FIGS. 4A-4C) contained on the conduit tube reverse connector 280a are able to sufficiently latch onto the annular locking protrusion 274a when the reverse connector 280a is attached to the tubular member 252a.

In other embodiments, when directly attached to the conduit tube 130, the first radial dimension corresponds to an inner radial dimension of a mount connector 134 of the conduit tube 130. In such configurations, the first radial dimension may be chosen to be equal to, or slightly greater than, the inner radial dimension of the mount connector 134 in order to provide an efficacious seal. In such configurations, because the first radial dimension is smaller than the second radial dimension, a directly connected conduit tube can abut the edge 268a formed at the intersection of both sections 266a, 270a.

In some embodiments, the changes in radial dimension about the conduit axis 202a along the outer surface 264a of the tubular member 252a are not as defined and abrupt. Rather, the radial dimension may remain constant throughout the length of the tubular member 252a or may gradually increase when moving along the length of the tubular member 252a from the end 254a toward the suction port 350a. In such an embodiment, a more efficacious seal can be formed, for example, by a friction fit, an interference fit, or a press fit. In some embodiments, other types of coupling mechanisms, such as a snap fit, a bayonet socket, threads, screws, tightening collars, retention collars, or other suitable mechanisms can also be used.

With continued reference to FIG. 3B, the interface port 300a of the mount body 210a can be similar in construction to the conduit port 250a. The interface port 300a can include a generally cylindrical tubular member 302a that is rotated about the interface axis 204a. A channel 310a, which can be centered along the interface axis 202a, can extend along the length of the tubular member 302a. The channel 310a of the interface port 300a can define the inner surface 312a of the tubular member 302a. In some embodiments, the channel 310a has a generally circular cross-sectional shape that tapers when moving from the end 304a of the tubular member 302a toward the suction port 350a. This tapering enables tubes inserted into the channel 310a to be subject to a decreasing radial dimension as the tubes are inserted. Such a decrease in radial dimension can provide a more efficacious seal.

In some embodiments, the radial dimension of the channel 310a remains generally constant throughout the length of the channel 310a. In yet other embodiments, the radial dimension of the channel 310a increases when moving from the end 304a of the tubular member 302a toward the suction port 350a. The radial dimension of the channel 310a and the degree of tapering, if any, of the channel 310a can be dependent upon the desired flow characteristics through the flow channel 212a of the mount body 210a as well as considerations regarding sealing for tubes inserted into the channel 310a. Furthermore, other embodiments of the mount body 210a have channels 310a of different cross-sectional shapes such as, but not limited to, ovals, ellipses, or polygons. In some embodiments, the channel 310a is offset from the interface axis 204a.

As with the conduit port 250a, in some embodiments, the inner surface 312a of the tubular member 302a can be relatively smooth with no protrusions or other abrupt changes in diameter. Presence of protrusions or other abrupt changes in diameter could potentially accelerate the accumulation of condensate, secretions, and other matter by obstructing flow and providing a surface upon which such condensate, secretions, and other matter can collect. In some embodiments, such protrusions along the inner surface 312a may exist for other beneficial purposes such as, but not limited to, coupling mechanisms for either the interface tube reverse connector 330a or the interface tube 140. For example, in embodiments where the interface tube 140 is directly attached to the tubular member 302a of the mount body 210a, the mount end of the conduit tube 140 may be a male connector that is inserted into the channel 310a. Under such circumstances, it could potentially be beneficial to include an annular protrusion on the inner surface 312a to provide a more advantageous seal and to prevent accumulation of condensates, secretions, and materials on the tip of the interface tube 140. Such an annular protrusion can also be used with the interface tube reverse connector 330a, which has an inner tubular member 424 that is inserted into the channel 310a.

In some embodiments of the angled catheter mount 200a, the outer surface 314a of the tubular member 302a can have multiple protrusions that are configured to attach to the conduit tube reverse connector 330a or the mount end 144 of the interface tube 140. Moving from the end 304a of the tubular member 302a toward the intersection area 214a, the outer surface 314a can have an annular slot 316a, an intermediate annular protrusion 320a, an annular locking protrusion 324a, and an annular depression 328a. Annular slot 316a, intermediate annular protrusion 320a, annular locking protrusion 324a, and annular depression 328a can have radial dimensions about the interface axis 204a. These radial dimensions can be similar to those of the conduit port 250a; however, the radial dimensions may differ depending on the connectors used. In some embodiments, the radial dimensions of the two ports can be equivalent to ensure the interchangeability of the two reverse connectors 280a, 330a. In some embodiments, the radial dimensions are different due to differences in the designs of the reverse connectors 280a, 330a. Furthermore, in some embodiments, the tubular members 252a, 302a may have cross-sectional shapes that differ from circles. Other non-limiting examples of other cross-sectional shapes can include ovals, ellipses, and polygons such as squares, pentagons, and hexagons.

Reverse Connectors

Figure 4A:
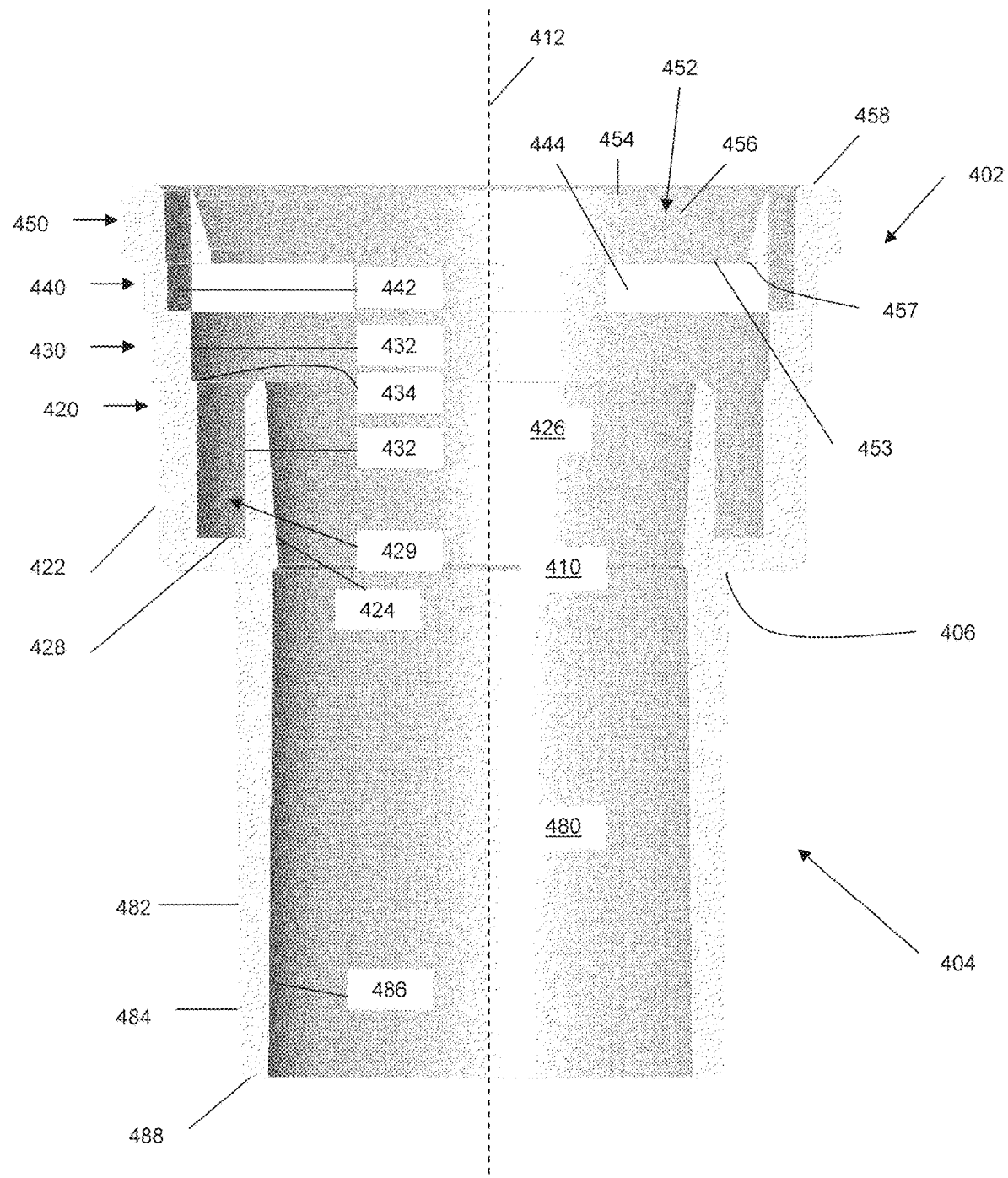
FIG. 4A is a section view of another catheter mount that is arranged and configured in accordance with certain features, aspects and advantages of the present invention.
Figure 4B:
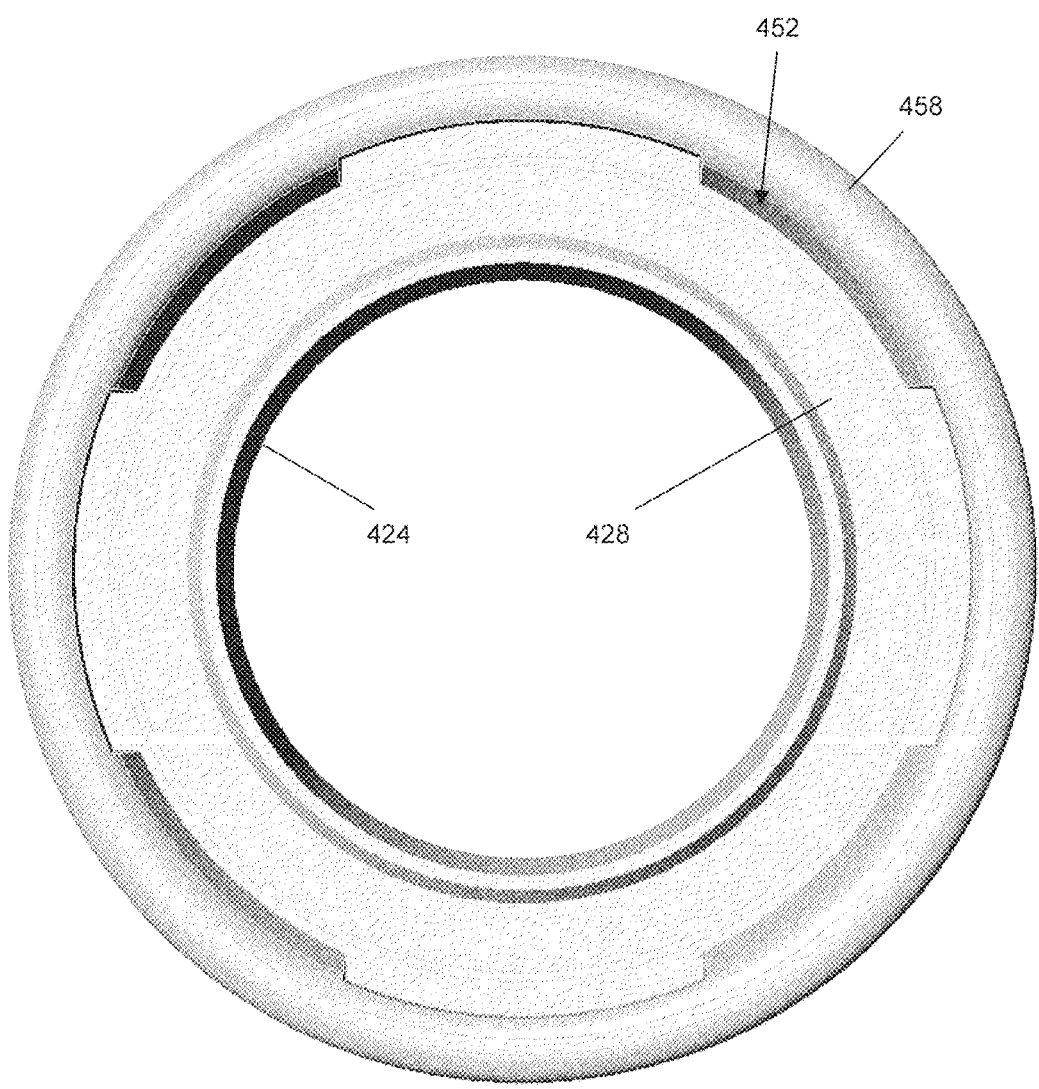
FIG. 4B is an end view of the catheter mount of FIG. 4A.

FIGS. 4A through 4B are illustrations of a reverse connector that can be used with the catheter mounts described herein. For purposes of illustration, the description below will be in reference to the conduit tube reverse connector 280a shown in combination with the angled catheter mount 200a in FIG. 2A, which may be reversibly attached to the tubular member 252a (see FIG. 3B) of the conduit port 250a. The design of the interface tube reverse connector 330a can be similar to that of the conduit tube reverse connector 280a. As such, the description contained herein is also applicable to the interface tube reverse connector 330a and the reverse connectors of other embodiments, although the shapes and dimensions would correspond to the interface port 300a rather than the conduit port 250a. In addition, the design of the conduit and interface tube reverse connectors for other embodiments of the catheter mount, such as, but not limited to, the dual-valve catheter mount 200b, the switch catheter mount 200c, and the wide-range valve catheter mount 200d, are also similar to that of the conduit tube reverse connector 280a. As such, the description contained herein, is also applicable to the design of the conduit and interface tube connectors for such other embodiments.

In some embodiments, the conduit tube reverse connector 280a is manufactured from the same materials as that of the mount body 210a. In some embodiments, the conduit tube reverse connector 280a is manufactured from materials that allow for the formation of a more advantageous seal, such as more elastic materials, when adjacent to another surface. Embodiments may be manufactured from materials, such as, but not limited to, plastics such as polyvinyl chloride, metals such as brass, stainless steel, and titanium, rubbers, or other polymers or composites.

The reverse connector 280a has both a mount connector 402 configured to be reversibly attached to the mount body 210a and a tube connector 404 configured to be reversibly attached to the conduit tube 130, such as an intermediate tube. These connectors 402, 404 meet at intersection 406. The reverse connector 280a is configured to allow fluid communication between both the mount connector 402 and the tube connector 404 via a flow channel 410 comprised of the channel 426 of the mount connector 402 and the channel 480 of the tube connector 404. The shape of the mount connector 402 generally corresponds to the outer surface 264a of the tubular member 252a. As such, when moving along the length of the mount connector 402 from the intersection 406 to the end 458 of the mount connector 402, the mount connector 402 has a slot receiving section 420, an intermediate seat section 430, a neck section 440, and an interlock section 450. In the illustrated embodiment, the components of the reverse connector 280a are generally cylindrical and formed about a central longitudinal axis 412. However, in other embodiments, the reverse connector could take on other shapes based on the shape of the tubular member 252a and the shape of the mount connector 134.

At the slot receiving section 420, the mount connector 402 is comprised of an outer tubular member 422, an inner tubular member 424, and an annular seat 428. In this configuration, an annular space 429 is defined between the inner surface 423 of the outer tubular member 422, the outer surface 425 of the inner tubular member 424, and the seat 428. The annular space 429 can be sized to receive the annular slot 266a and, in some embodiments, provides a generally hermetic seal to reduce the likelihood of entry of outside air into the mount body 210a. As such, the annular space 429 can have the same dimensions of the annular slot 266a or, in other embodiments, can be smaller. The dimensions can be based upon the type of material being used, the amount of sealing desired, and the amount of force desired to insert and remove the mount connector 402 from the tubular member 252a. In some embodiments, upon insertion of the annular slot 266a into the annular space 429, the end 254a of the tubular member 252a can be pressed against the annular seat 428 to provide a more efficacious seal. In some embodiments, the inner tubular member 424 can be tapered at its end to facilitate insertion into the channel 260a of the conduit port 250a.

The intermediate seat section 430 generally can correspond to the dimensions of the intermediate annular protrusion 270a of the tubular member 252a. In some embodiments, the radial dimension of the inner surface 432 about the longitudinal axis 412 is equal to, or slightly less than, the radial dimension of the intermediate annular protrusion 270a about the conduit axis 202a. As such, when the conduit tube reverse connector 280a is attached to the mount body 210a, the intermediate annular protrusion 270a of the tubular member 252a and the inner surface 432 of the reverse connector 280a may provide an additional seal. In some embodiments, the radial dimension of the inner surface 432 may be slightly greater than the radial dimension. For example, this may be the case when the seal provided at the connection between the annular slot 266a and the slot receiving section 420 is deemed sufficient. Under such circumstances, the radial dimension of the inner surface 432 of the intermediate seat section 430 may provide little interference and thus allow a user of the mount to more easily connect the conduit tube reverse connector 280a to the tubular member 252a. In some embodiments, when the conduit tube reverse connector 280a is attached to the mount body 210a, the edge 434 formed at the intersection of the intermediate seat section 430 and the slot receiving section 420 abuts the edge 268a on the tubular member 252a.

The neck section 440 generally corresponds with the dimensions of the annular locking protrusion 274a of the tubular member 252a. In some embodiments, the radial dimension of the inner surface 442 about the longitudinal axis 412 is generally equal to, or slightly greater than, the radial dimension of the annular locking protrusion 274a about the conduit axis 202a. The neck section 440 can be configured to deform more freely compared to other sections of the mount connector 402, particularly when the reverse connector 280a is in the process of being attached to the tubular member 252a of the mount body 210a. As will be discussed in greater detail with respect to the interlock section 450, deformation of the mount connector 402 can occur as the interlock ramps 452 encounter and slide across the annular locking protrusion 274a. As such, this deformation can be facilitated by having the neck section 440, which is adjacent to the interlock section 450, have greater flexibility.

In some embodiments, the radial thickness of the neck section 440a about the longitudinal axis 412 is less than the radial thickness of the other sections of the mount connector 402. The reduced thickness, particularly when an elastic material is used for the reverse connector 280a, increases the flexibility of the section 440. In some embodiments, a plurality of spaced apertures 444 can be included along the circumference of the neck section 440. In the embodiment shown in FIG. 4A, four equally spaced apertures 444 can be formed with a generally rectangular shape. In some embodiments, more apertures may be used that have a smaller cross-sectional area. In some embodiments, fewer apertures may be used that have a larger cross-sectional area. Any shape, such as ellipses, ovals, or other polygons, may be used for the apertures and any number of such apertures may be placed along the circumference of the neck section 440 taking into consideration the desired structural integrity of the reverse connector 280a and the amount of flexibility sought in the neck section 440. In some cases, no such apertures 444 are used because the reduced thickness of the neck section 440 may be sufficient to provide the required flexibility. In some embodiments, more apertures may be used because the neck section 240 does not have a reduced thickness.

The interlock section 450 generally corresponds with the dimensions of the annular depression 278a of the tubular member 252a. The interlock section 450 can be configured to lock the reverse connector 280a with the tubular member 252a via the annular locking protrusion 274a. As such, in some embodiments, the interlock section 450 can include a plurality of interlock ramps 452 that are configured to contact and slide across the outer surface of the locking protrusion 254 and that can serve as the connection mechanism. In some embodiments, the interlock ramps 452 can have a generally triangular cross-section along a plane that extends parallel to and that runs through the longitudinal axis 412. The interlock ramps 452 can taper from the trailing edge 453 to the leading edge 454. As such, the radial dimension of the leading edge 454 of the interlock ramps 452 about the longitudinal axis 412 can be substantially equivalent to the radial dimension of the inner surface of the interlock section 450 about this axis 412. In some embodiments, the radial dimension of the trailing edge 453 about the longitudinal axis 412 can be substantially less than that of the leading edge 452 forming locking edges 457.

During operation, when the reverse connector 280a is attached, the leading edges 452 of the interlock ramps 452 can contact the annular locking protrusion 274a. As the tubular member 252a is inserted further into the mount connector 402 of the reverse connector 280a, the mount connector 402 deforms in response to the increased force caused by contact between the outer surface the annular locking protrusion 274a and the contact surface 456 of the interlocking ramps 452 caused by the decrease in radial dimension towards the trailing edge 453. Upon being fully inserted, the mount connector 402 returns substantially to its original shape and the locking edge 457 abuts the corresponding locking edge 276a of the tubular member 252a.

In some embodiments, there are four interlocking ramps 452. In some embodiments, there may be a greater number of such ramps or a lesser number of ramps 452 as desired. In some embodiments, in lieu of the locking ramps 452, other cross-sectional shapes such as spherical domes or raised ridges can be used to secure the reverse connector 280a to the tubular member 252a. In some embodiments, the structure may use threads, bayonet collars, or slot connectors for connection onto the mount body 210a.

With continued reference to FIG. 4A, the tube connector 404 has a generally cylindrical tubular member 482 formed around the longitudinal axis 412 with the channel 480 running therethrough. In the illustrated embodiment, the channel 480 defines the inner surface 486, which tapers moving from the end 488 of the tube connector to the intersection 406. In some embodiments, the inner surface 486 can have a generally constant radial dimension about the longitudinal axis 412 throughout the length of the tubular member 482. In some embodiments, the radial dimension about the longitudinal axis 412 can increase when moving from the end 488 toward the intersection 406. In some embodiments, the outer surface 482 can be of relatively constant radial dimension and can be configured to receive a mount connector 134 from the conduit tube 130. Some embodiments of the reverse connector 280a can have outer surfaces 482 that increase in radial dimension whereas some embodiments may decrease in radial dimension. In some embodiments, a generally hermetic seal can be formed, for example, by a friction fit, interference fit, or press fit. In some embodiments, other types of coupling mechanisms, such as a snap fit, a bayonet socket, threads, screws, tightening collars, retention collars, or other similar mechanisms can be used.

Suction Port of Angled Catheter Mount

Referring back to FIG. 3B, the suction port 350a of the angled catheter mount 200a can comprise an opening 360a on the outer surface 370a of the suction port 350a. The opening 360a can be configured to allow insertion of a suction catheter 160 into the mount body 210a and into the flow channel 212a. In some embodiments, the opening 360a is circular. In some embodiments, the opening 360a may be of different shapes such as ovals, ellipses, and polygons. Circumscribing the opening 360a is engagement lip 362a that is configured to be received within an annular locking slot 520 of the valve 380a.

As illustrated in FIGS. 2C and 2D, a desired placement of the single opening 360a allows the suction catheter 160 to access both, as illustrated in FIG. 2C, the interior of the conduit port 250a and possibly any attached tubing and, as illustrated in FIG. 3D, the interior of the interface port 300a and possibly any attached tubing. Therefore, placement of the opening 360a advantageously allows direct access to both tubes without having to remove the catheter mount 200a from the system. Such a configuration reduces the amount of time necessary in maintaining the interior surfaces of a respiratory assistance system, such as those or the part thereof shown in FIGS. 1A-1C, since the catheter mount 200a need not be removed from the system for routine removal of condensate or the like.

In some embodiments, the opening 360a is opposite the interface port 300a and is centered on the interface axis 204a. In some embodiments, the opening 360a is parallel to a plane that is generally perpendicular to the interface axis 204a. As such, in the illustrated embodiment, the opening angle $O_a$ is equal to about 90°. In some embodiments, the opening angle $O_a$ can range from about 70° to about 160°. In some embodiments, the opening angle $O_a$ can range from about 75° to about 130°. In some embodiments, the opening angle $O_a$ can range from about 80° to about 100°. The opening angle $O_a$ may vary based on other design features, such as, but not limited to, the intersection angle $I_a$, the offset distance $D_a$ from the conduit axis 202a, and the offset distance $H_a$ from the interface axis 204a, and the like as described in more detail below.

Additionally, in some embodiments, there can be an offset distance $D_a$, defined as the distance between the conduit axis 202a and an axis parallel to the conduit axis 202a running through the center of opening 360a. This offset distance $D_a$ can allow a conduit tube 160 sufficient space to access the conduit port 250a. In some embodiments, the offset distance $D_a$ varies from about 0.1 cm to about 6.0 cm. In some embodiments, the offset distance $D_a$ can vary from about 0.5 cm to about 3.0 cm. In some embodiments, the offset distance $D_a$ can vary from about 0.5 cm to about 1 cm. In some embodiments, the offset distance can be equal to about 0.7 cm. The offset distance $D_a$ can vary based on other design features, such as, but not limited to, the opening angle $O_a$, the intersection angle $I_a$, and the offset distance $H_a$ from the interface axis 204a, and the intended application. The offset distance $D_a$ may be about 0.7 cm for an adult catheter mount and about 0.36 cm for an infant catheter mount, for example.

In some embodiments, there is an offset distance $H_a$, defined as the distance between the interface axis 204a and an axis parallel to the interface axis 204a tangential to the uppermost part of the opening 360a. This offset distance $H_a$ can allow a conduit tube 160 sufficient space to access the conduit port 250a. In some embodiments, the offset distance $H_a$ varies from about 0.2 cm to about 1.0 cm. In some embodiments, the offset distance $H_a$ can vary from about 0.4 cm to about 0.8 cm. In some embodiments, the offset distance $H_a$ can vary from about 0.5 cm to about 0.7 cm. In some embodiments, the offset distance can be equal to about 0.58 cm. The offset distance $H_a$ can vary based on other design features, such as, but not limited to, the opening angle $O_a$, the intersection angle $I_a$, and the offset distance $D_a$ from the conduit axis 202a, and the intended application. The offset distance $H_a$ may be 0.58 cm for an adult catheter mount and about 0.35 cm for an infant catheter mount, for example.

The intersection of the conduit axis 202a and the interface axis 204a form an intersection angle $I_a$ which in a preferred embodiment, is an acute angle. In some embodiments of the angled catheter mount 200, the intersection angle $I_a$ ranges from about 35° to about 90°. In some embodiments, the intersection angle $I_a$ ranges from about 50° to about 85°. In some embodiments, the intersection angle $I_a$ ranges from about 65° to about 80°. In some embodiments, the intersection angle $I_a$ is about 75°. The offset distance $H_a$ can vary based on other design features, such as, but not limited to, the opening angle $O_a$, the offset distance $D_a$ from the conduit axis 202a, and the offset distance $H_a$ from the interface axis 204a.

As a non-limiting example, in other embodiments, the opening 360a may be raised vertically along the outer surface 370a, thereby increasing the offset distance $H_a$ as the opening angle $O_a$ is increased or decreased from 90°. In some embodiments, the offset distance $H_a$ and/or $D_a$ can be reduced as the intersection angle $I_a$ is decreased. Furthermore, the opening 360a is not limited to placement opposite the interface section 300a. In some embodiments, the opening 360a may be placed opposite the conduit section 204 with the same general placement principals being applicable.

Valve for Suction Port

Figure 5A:
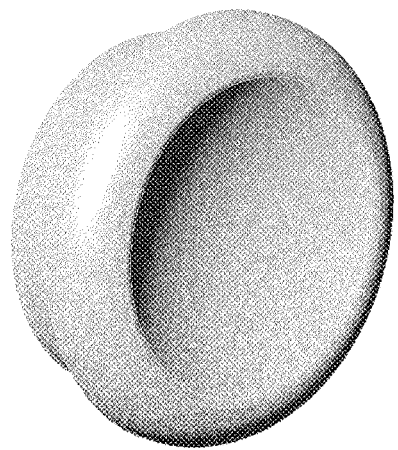
FIG. 5A is perspective view of a valve used with the catheter mount of FIG. 2A.
Figure 5B:
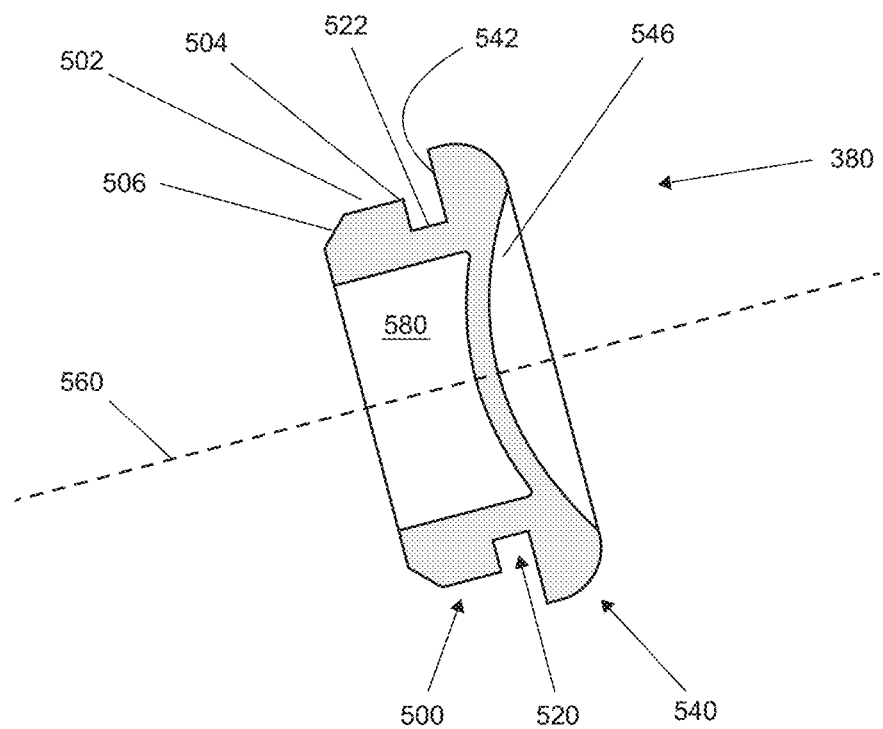
FIG. 5B is a sectioned view of the valve of FIG. 5A.

In order to provide a generally hermetic seal when a suction catheter 160 is not being used, a valve 380a can be provided and received within the opening 360a of the suction port 350a. FIGS. 5A-5B are illustrations of an embodiment of the valve 380a which can be placed in the opening 360a. The design of the valves for other embodiments of the catheter mount, such as, but not limited to, the dual-valve catheter mount 200b and the switch catheter mount 200c, are similar to that of the valve 380a. As such, the description contained herein, can be applicable to the design of the valves for such other embodiments.

The valve 380a can be manufactured from any suitable materials. In some embodiments, the valve 380a can be manufactured from materials with sufficient elasticity such that the valve 330a can deform and conform to the shape of the opening 360a to provide a more effective seal.

Referring to FIG. 5B, the valve 380a has an insertion member 500, an annular locking slot 520, an end cap 540, and inner channel 580. In the illustrated embodiment, the valve 380a has a generally circular shape rotated about a central longitudinal axis 560. The insertion member 500 is configured to be received within the mount body 210a when fully assembled. In some embodiments, the radial dimension of the outer surface 502 at the trailing end 504 of the insertion portion 500 about the longitudinal axis 560 is greater than the radial dimension of the opening 360a. In order to facilitate insertion of the insertion portion 500 into the opening 360a due to the differences in size, the insertion portion 500 is preferably tapered at the leading end 506. In some embodiments, the radial dimension of the outer surface 502 at the leading end 506 is equal to, or slightly less than, the diameter of opening 360a.

The annular locking slot 520 can be configured to reduce the likelihood of undesired movement of the valve 380a when the valve has been attached to the mount body 210a. The dimensions of the annular locking slot 520 generally correspond to the dimensions of the engagement lip 362a. As such, the radial dimension of the outer surface 522 of the locking slot 520 is generally equal to, or slightly greater than, the radial dimension of opening 360a. The radial dimension of the outer surface 522 can be sized slightly greater than the radial dimension of the opening 360a in order to provide a more airtight seal. In some embodiments, the width of the locking slot 520 in the longitudinal direction may be equal to, or slightly less than, the width of the engagement lip 362a. The size of the annular locking slot 520 can be based upon the amount of sealing required, the elasticity of the material, and any concerns of ease of placement and replacement.

The end cap 540 can be configured to control fluid communication through the inner channel 560. End cap 540 can be comprised of a generally flat surface 542 configured to abut the outer surface 370a of the suction port 350a when the valve is fully inserted within the mount body 210a. In the illustrated embodiment, the end cap 540 can be tapered from the leading edge to the trailing edge. Other embodiments need not have the reduction in diameter and can be tapered or of constant diameter.

In the illustrated embodiment, the end cap has detent 546 configured to allow insertion of a suction catheter 160 or the like. Such detent may include a slit. In some configurations, the slit extends the center of the detent to allow a suction catheter 160 to be inserted into the valve 380a and into the inner channel 580 without the need to remove the valve 380a. In some configurations, the slit runs generally vertically such that the catheter can be moved along at least a portion of the slit in a generally vertical direction. When a suction catheter 160 is removed from the slit, the slit can return to its original shape and provide a generally hermetic seal.

Dual Valve Catheter Mount

Figure 6A:
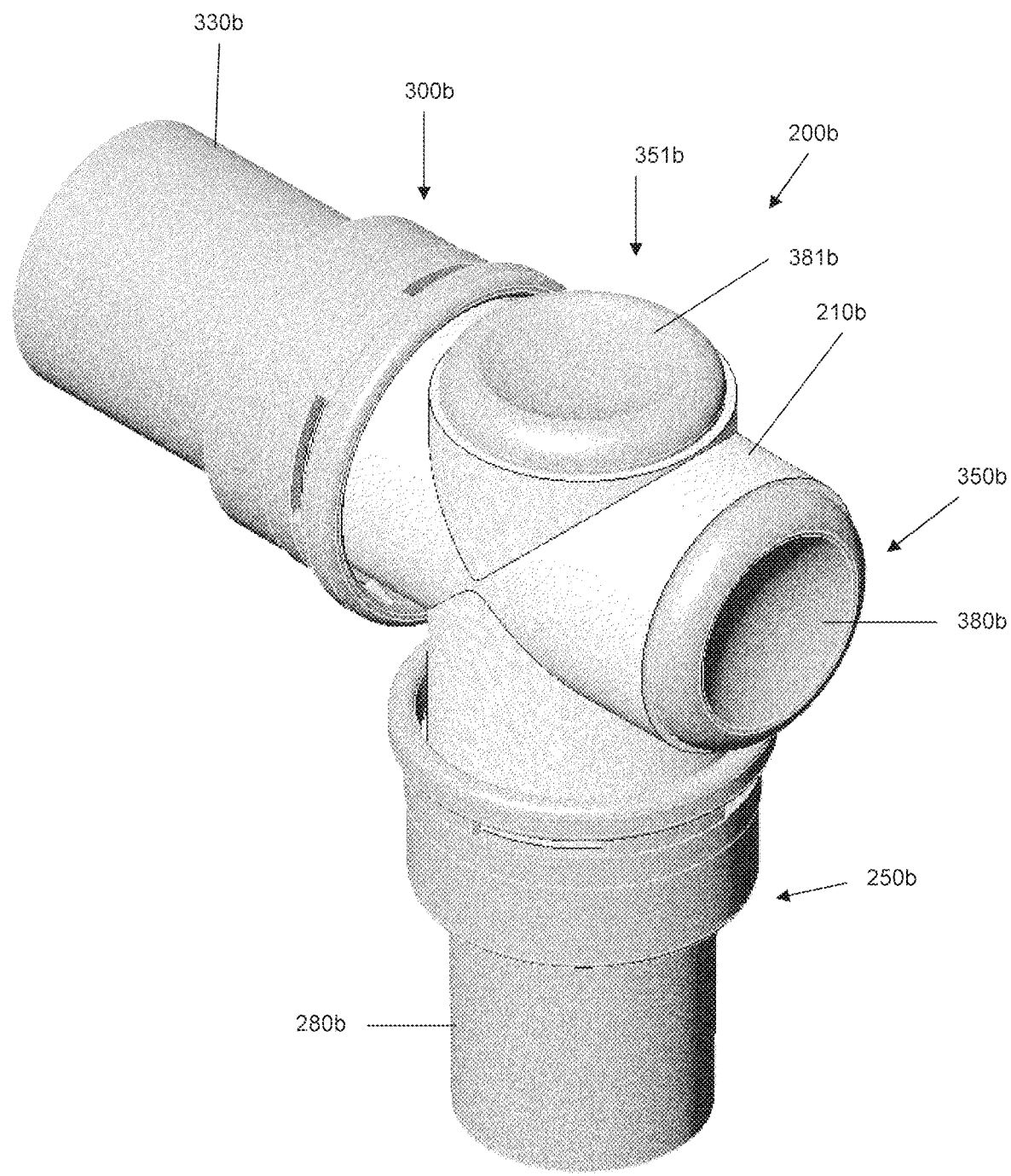
FIG. 6A is a perspective view of a further catheter mount that is arranged and configured in accordance with certain features, aspects and advantages of the present invention.
Figure 6B:
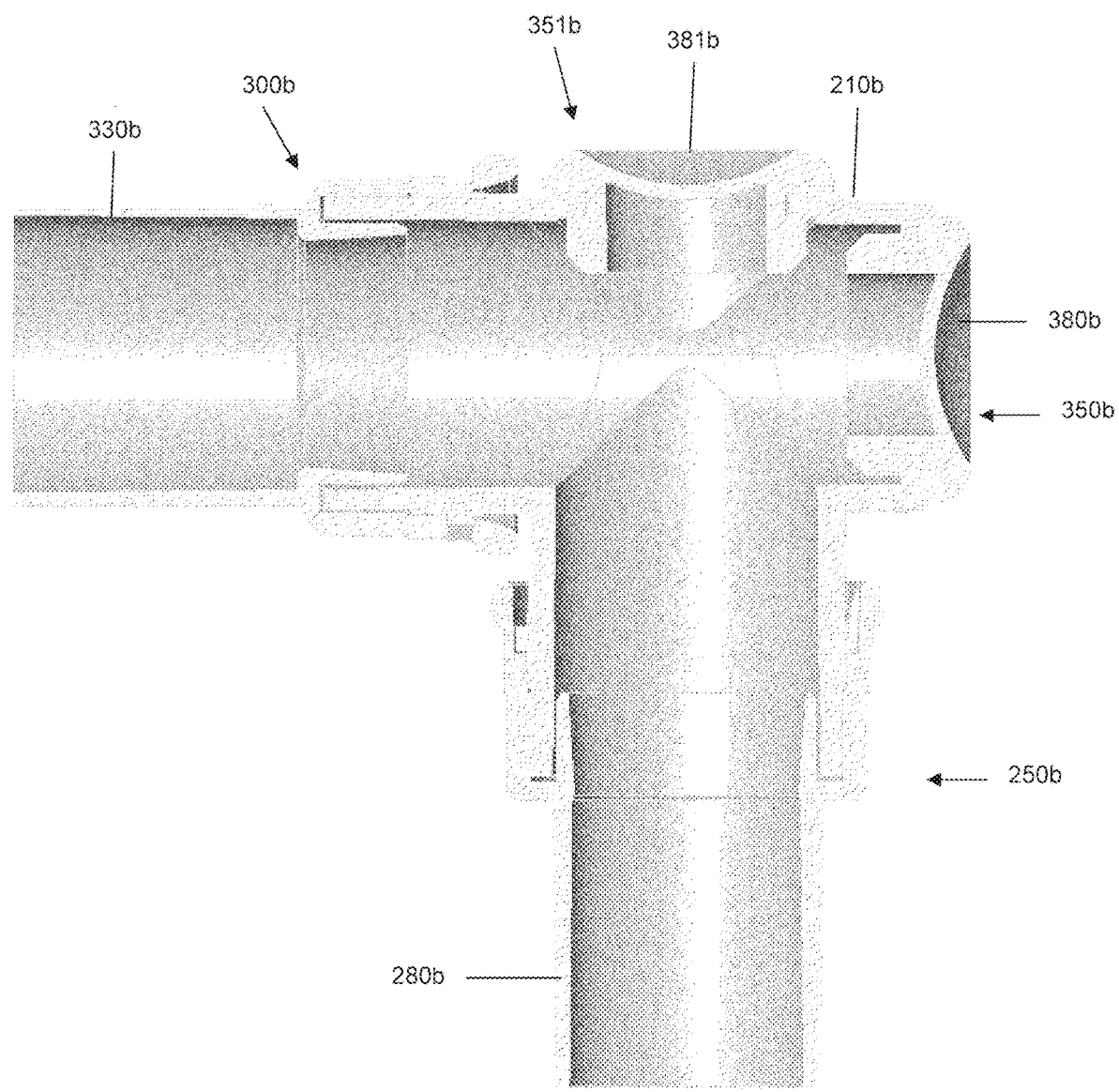
FIG. 6B is a section view of the catheter mount of FIG. 6A.
Figure 6C:
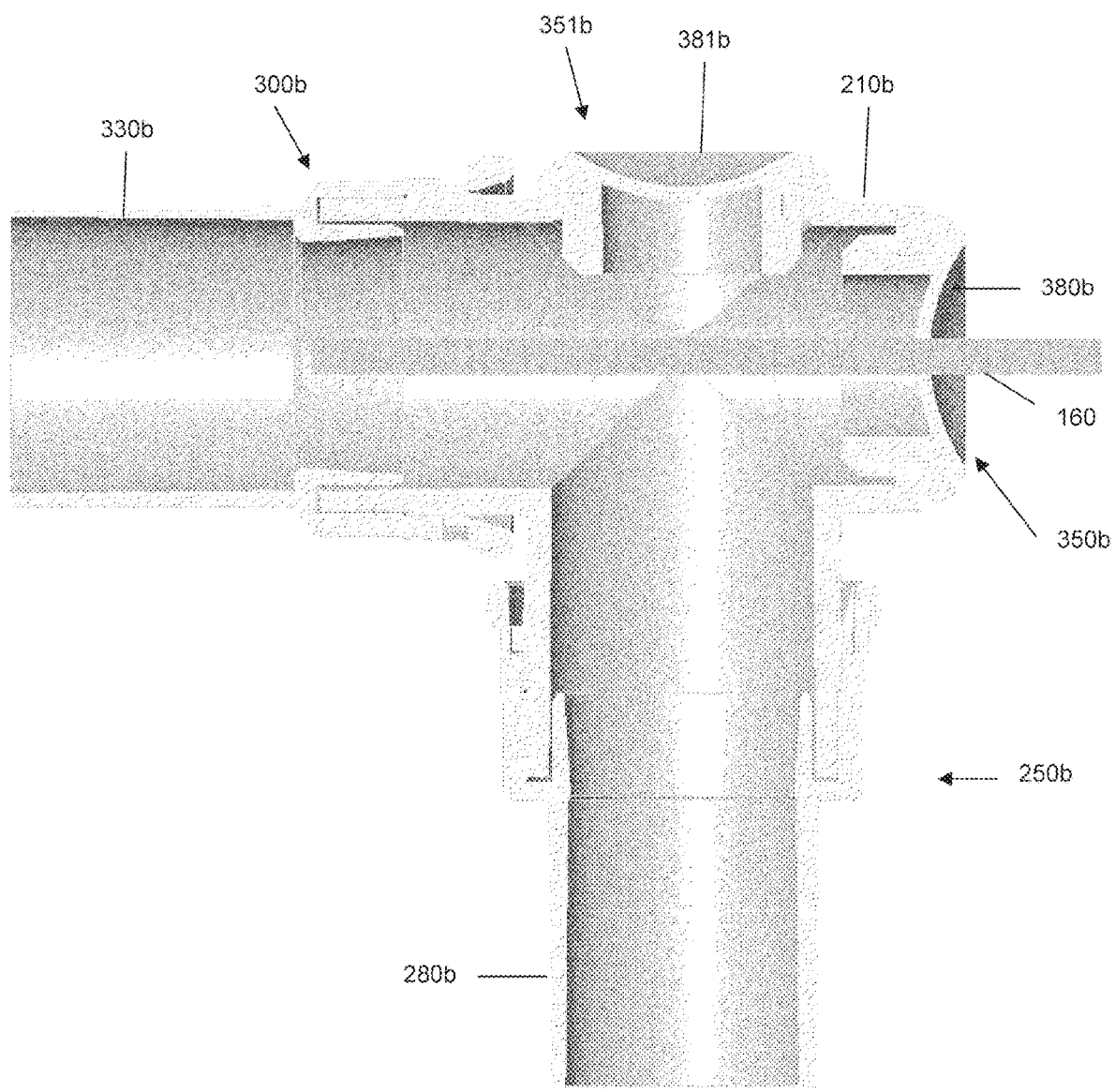
FIG. 6C is a section view of the catheter mount of FIG. 6A showing a schematic suction tube inserted into a first portion of the catheter mount.
Figure 6D:
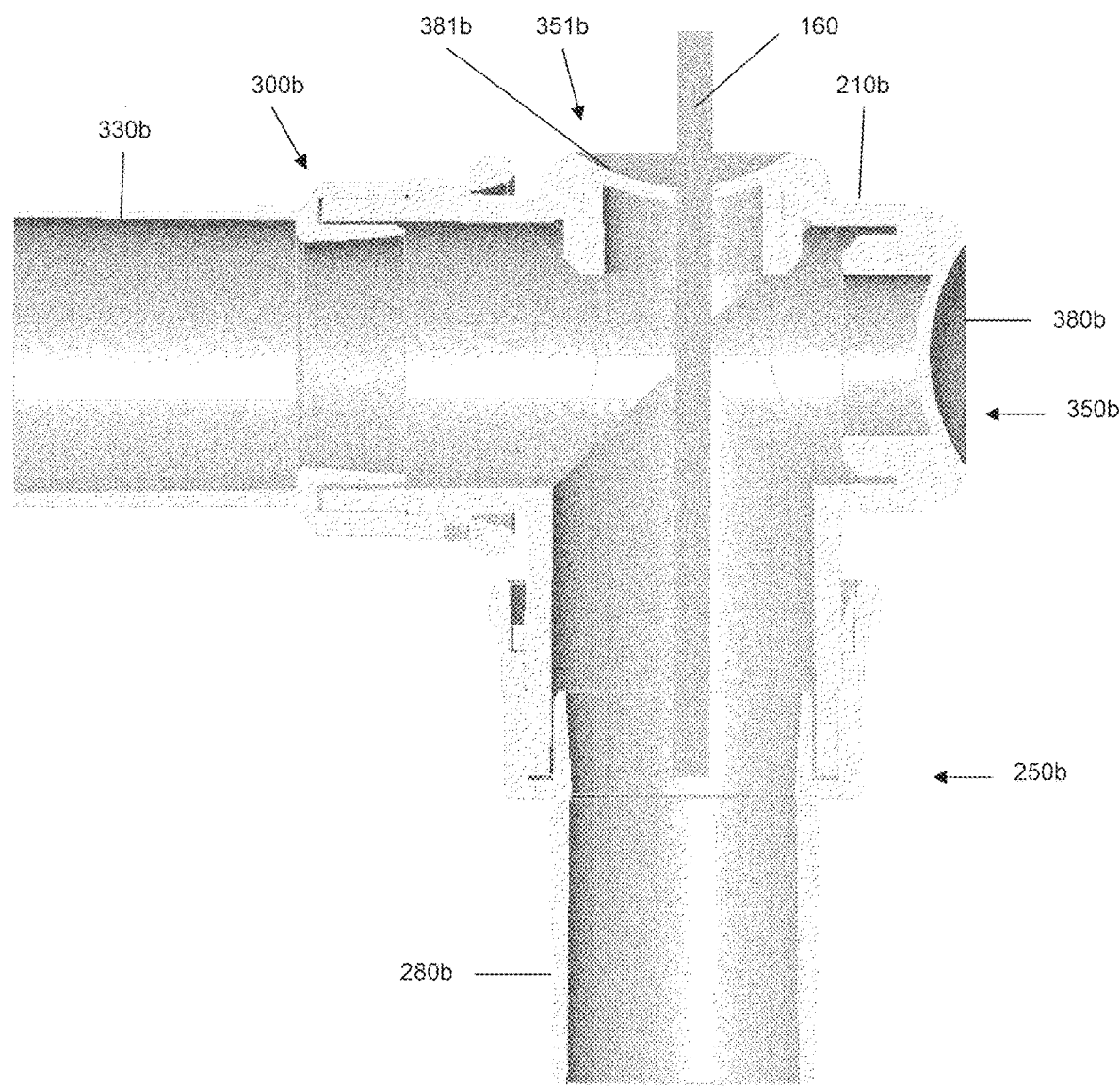
FIG. 6D is a section view of the catheter mount of FIG. 6A showing a schematic suction tube inserted into a second portion of the catheter mount.
Figure 7A:
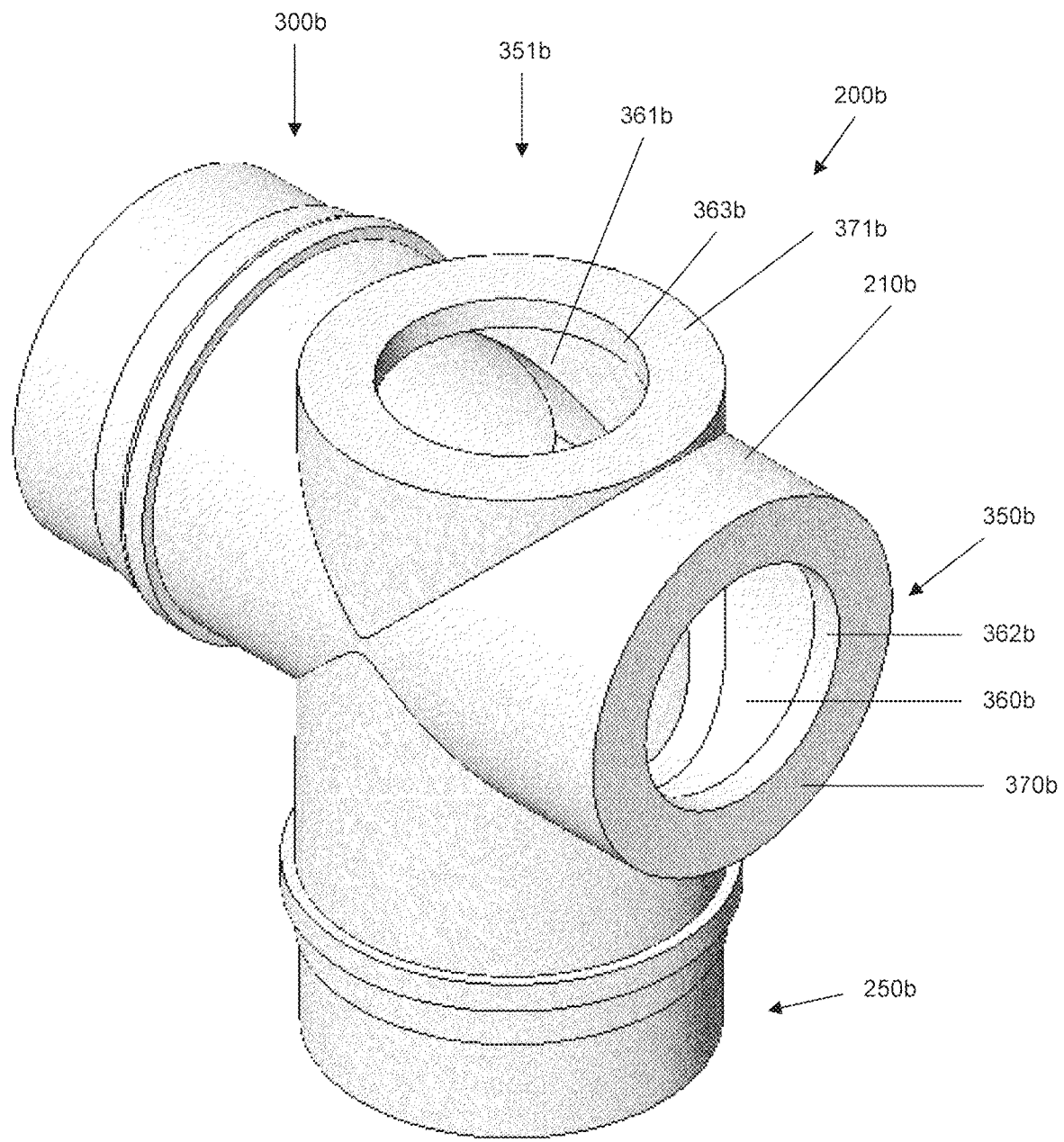
FIG. 7A is a perspective view of a further catheter mount that is arranged and configured in accordance with certain features, aspects and advantages of the present invention.

FIGS. 6-7 are illustrations of an embodiment of a dual-valve catheter mount 200b that is configured to allow a suction catheter 160 to access to both the conduit port 250b and the interface port 300b and possibly the corresponding tubes attached thereto due to the provision of two suction ports 350b, 351b. Dual-valve catheter mount 200b can be comprised of a conduit port 250b, an interface port 300b, and two suction ports 350b, 351b.

The dual-valve catheter mount 200b has a mount body 210b configured to allow fluid communication between the conduit port 250b and the interface port 300b via flow channel 212b. The construction of the dual-valve catheter mount 200b is similar to that of the angled catheter mount 200a with the main exception that the interface angle $I_a$ is 90° and that the catheter mount 200b includes a dual-suction port 350b, 351b design. As such, reference should be made to the description of the angled catheter mount 200a for a description of the components contained in the dual-valve catheter mount 200b such as those for the conduit port 250b, the interface port 300b, the design of the reverse connectors 280b and 330b as shown in FIGS. 4A-4B, and the design of the valves 380b and 381b as shown in FIGS. 5A-5B.

Figure 7B:
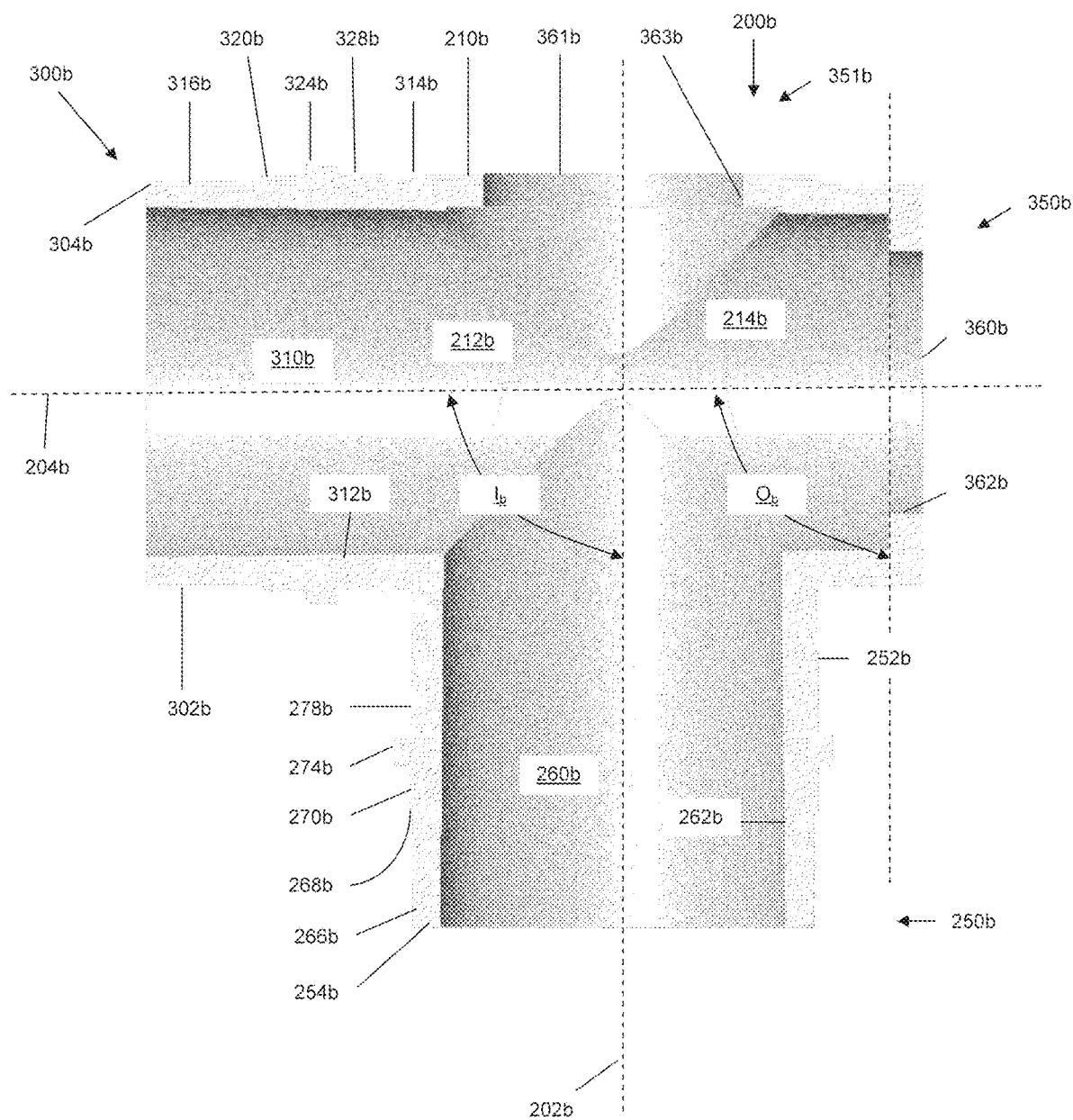
FIG. 7B is a section view of the catheter mount of FIG. 7A.

With reference to FIG. 7B, the dual-valve catheter mount 200b has a conduit suction port 351b directly opposite the conduit port 250b and an interface suction port 350b directly opposite the interface port 300b. Both the interface suction port 350b and the conduit suction port 351b have openings 360b, 361b respectively configured to permit insertion of a suction catheter 160 into the mount body 210b and into the flow channel 212b. In the illustrated embodiment, the suction ports 350b, 351b and the associated openings 360b, 361b have generally circular shapes that are centered about the conduit axis 202b and the interface axis 204b respectively. Furthermore, circumscribing the openings 360b, 361b are engagement lips 362b, 363b configured to be received within a locking slot 520 of the valves being used. In the illustrated embodiment, the size and shape of both ports 350b, 351b and their respective openings 360b, 361b are generally the same. In some embodiments, the size and shape of the ports may be dissimilar and may take on other shapes. For example, ports and openings may also be elliptical, such as an oval, or polygonal, such as a square, rectangle, pentagon, hexagon or the like.

In order to reduce the likelihood of interference between the valves used, in the illustrated embodiment, the interface suction port 350b is extended beyond the outer wall of tubular member 252b of the conduit port 250b. However, in the illustrated configuration, the conduit suction port 351b is not extended beyond the outer wall of tubular member 302b of the interface port 300b. In some embodiments, both of the suction ports 350b, 351b may be extended beyond the outer wall of the tubular members 302b, 252b in order to reduce the likelihood of interference or obstruction to flow within the fluid channel 212b of the mount body 210b. In some embodiments, both suction ports, 351b may not be extended beyond the outer wall of the tubular members 302b, 252b.

With reference to FIGS. 6C and 6D, placement of openings 361b, 360b allows the suction catheter 160 to access both, as illustrated in FIG. 6C, the interior of the conduit port 250b and possibly any attached tubing and, as illustrated in FIG. 6D, the interior of the interface port 300b and possibly any attached tubing. Therefore, placement of the openings 360b, 361b advantageously allows direct access to both tubes without removal of the catheter mount 200b from the system. Such a configuration reduces the amount of time necessary in maintaining the interior surfaces of a respiratory assistance system because the catheter mount 200b need not be removed from the system in order to perform routine maintenance.

In some embodiments, the intersection of the conduit axis 202b and the interface axis 204b form an intersection angle $I_b$. In some embodiments of the dual-valve mount 200b, the intersection angle $I_b$ could be any angle from about 30° to about 150°. In some embodiments, the intersection angle $I_b$ ranges from about 45° to about 135°. In some embodiments, the intersection angle $I_b$ ranges from about 70° to about 110°. Finally, in some embodiments, such as that illustrated in FIGS. 6-7, the intersection angle $I_b$ is about 90°. The intersection angle $I_b$ used for a particular embodiment of the dual-valve catheter mount 200b can be based on other design parameters such as, but not limited to, the offset angle $O_b$ and the placement of the two suction ports 350b, 351b.

Switch Catheter Mount

Figure 8A:
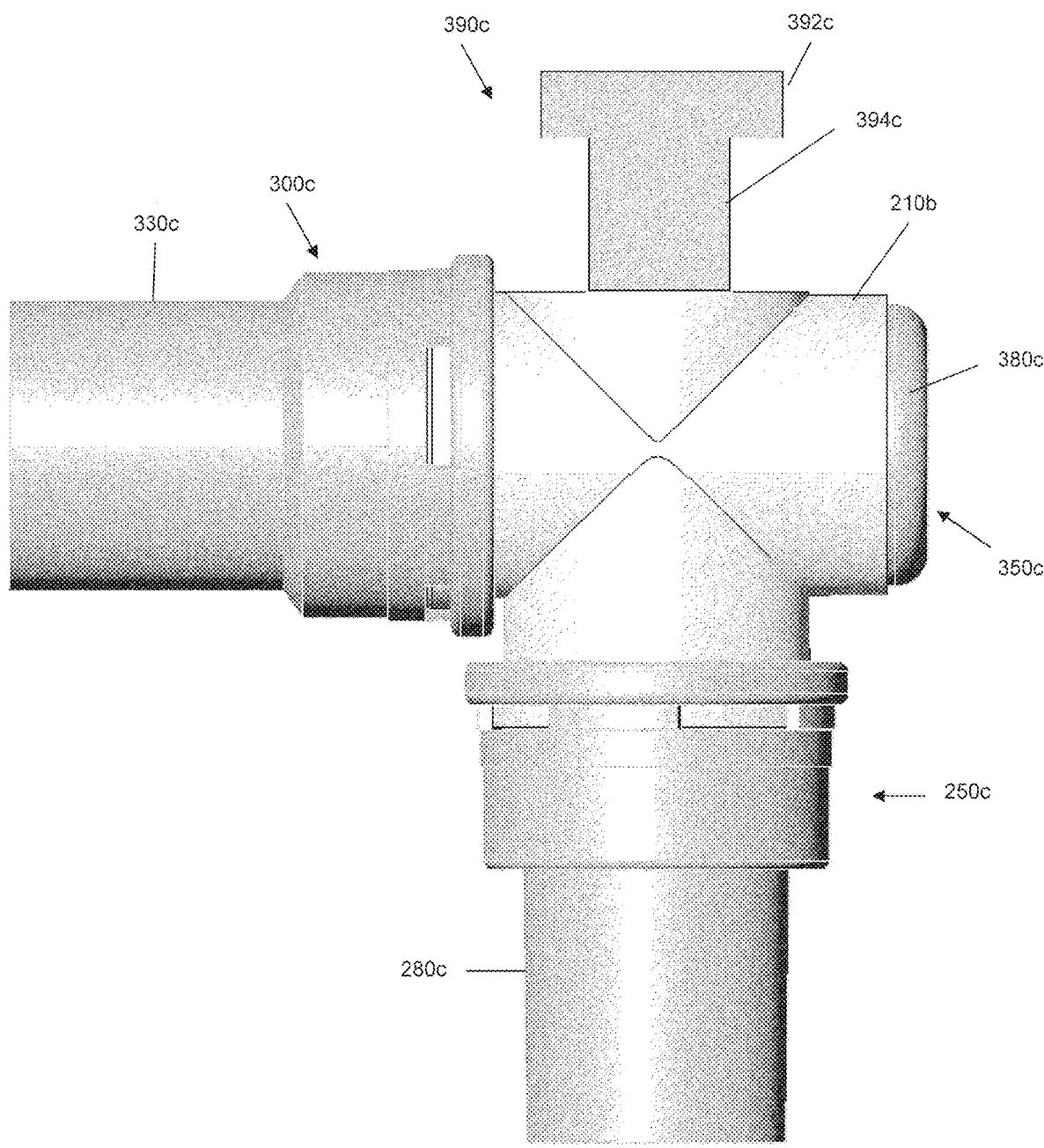
FIG. 8A is a side view of a catheter mount that is arranged and configured in accordance with certain features, aspects and advantages of the present invention.
Figure 8B:
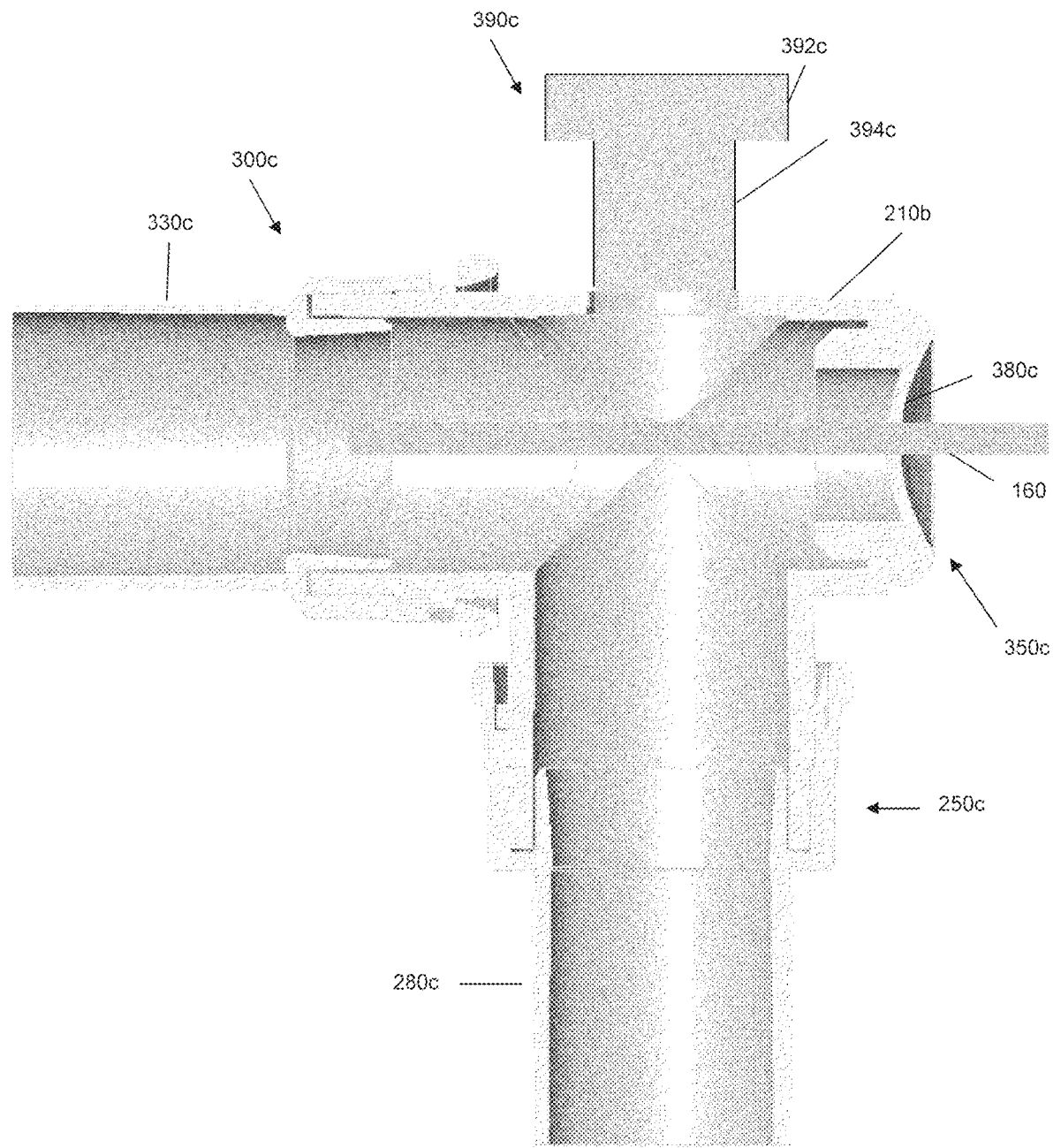
FIG. 8B is a section view of the catheter mount of FIG. 8A showing a schematic suction tube inserted into a first portion of the catheter mount.
Figure 8C:
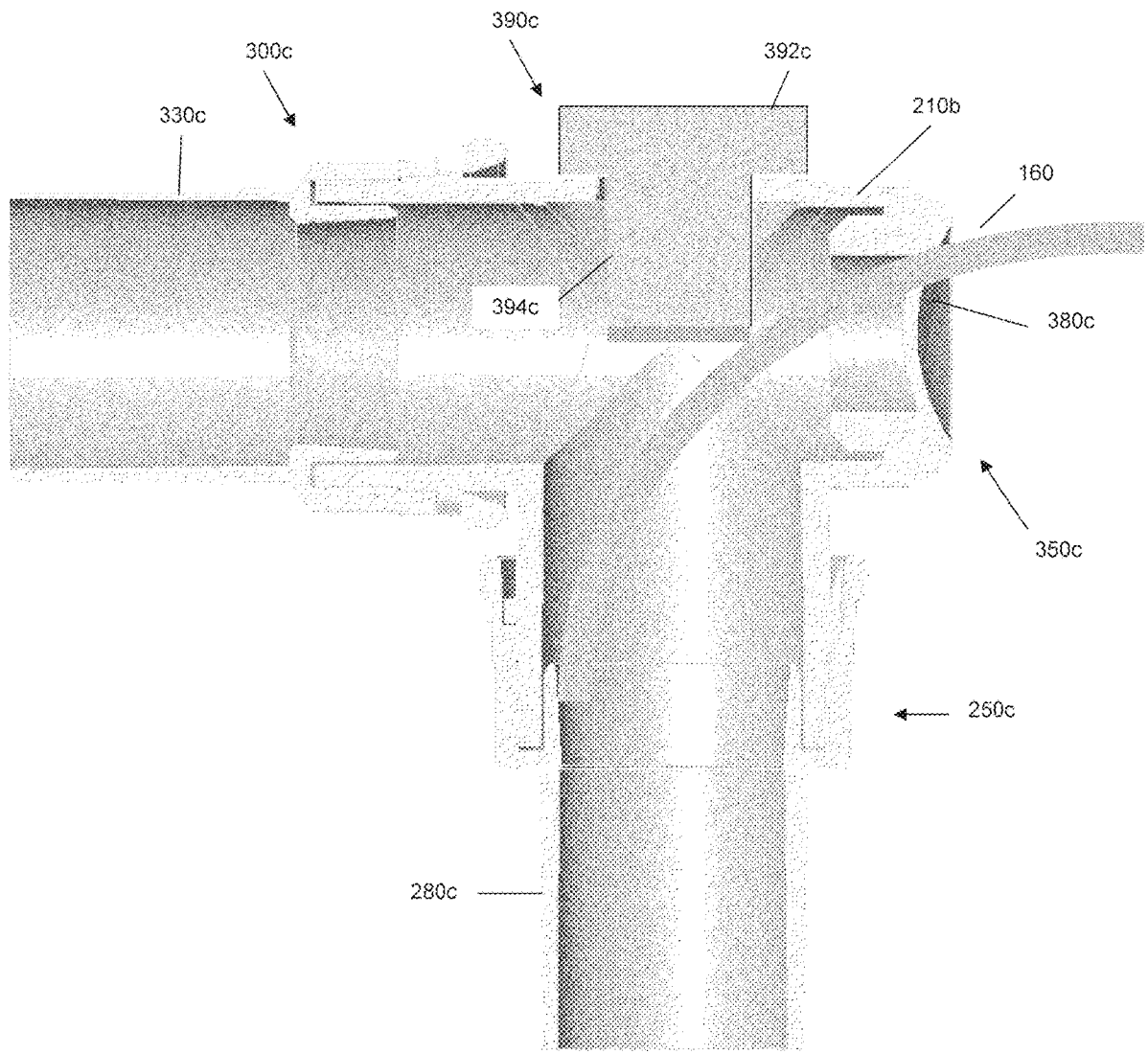
FIG. 8C is a section view of the catheter mount of FIG. 8A showing a schematic suction tube inserted into a second portion of the catheter mount.
Figure 9:
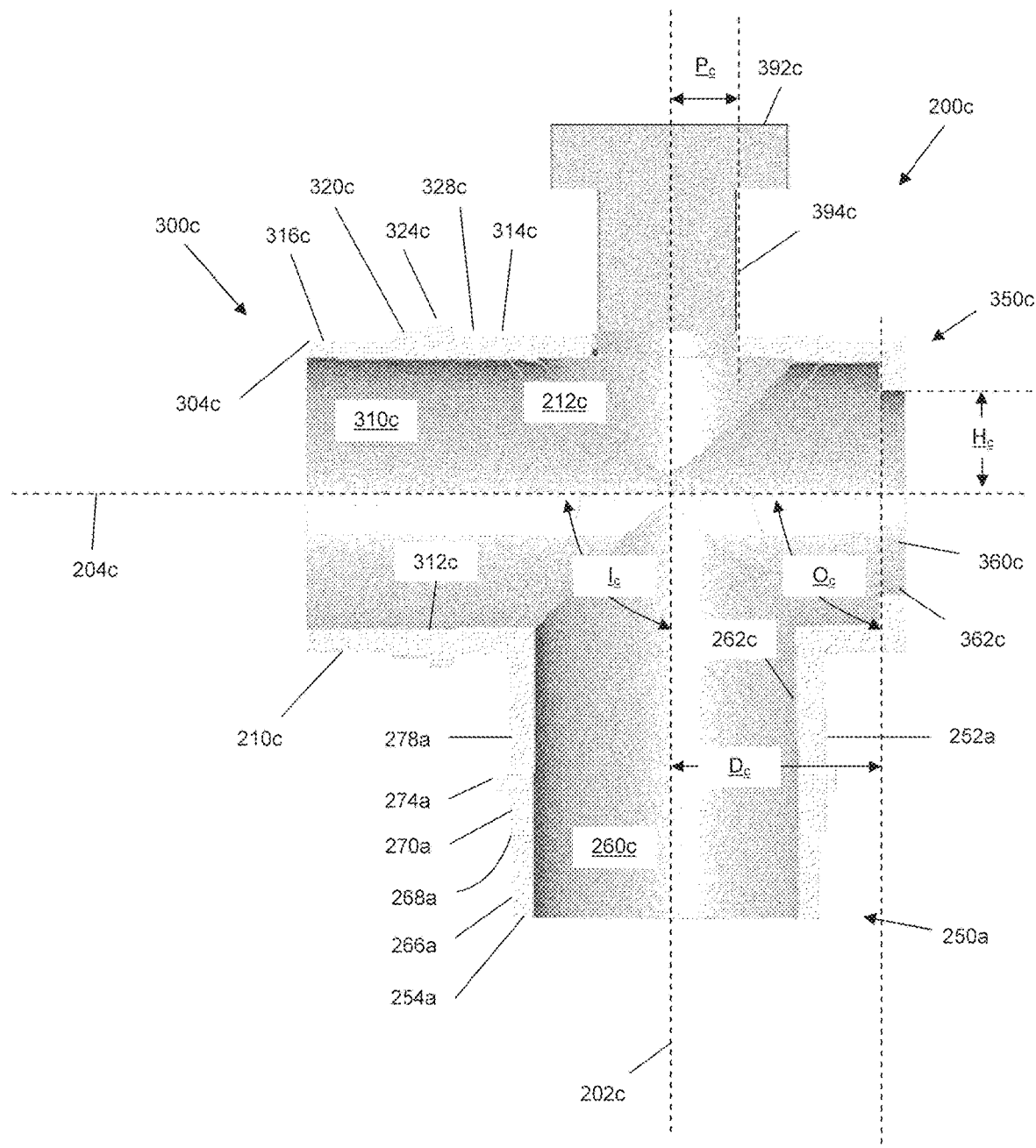
FIG. 9 is a section view of a portion of the catheter mount of FIG. 8A.

FIGS. 8-9 are illustrations of an embodiment of a switch catheter mount 200c that is configured to allow a suction catheter access to both the conduit port 250c and the interface port 300c and the corresponding tubes attached thereto due to the valve 380c and the switch 390c. The switch catheter mount 200c can comprise a conduit port 250c, an interface port 300c, and a suction port 350c. The switch catheter mount 200c has a mount body 210c configured to allow fluid communication between the conduit port 250c and the interface port 300c via the flow channel 212c. The construction of the switch catheter mount 200c can be similar to that of the dual-valve catheter mount 200b with the main exception that, rather than having a dual suction port design, the switch catheter mount 200c of the illustrated embodiment replaces one of the valves with a switch 390c. As such, reference should be made to the description of the dual-valve catheter mount 200b for a description of the components contained in the switch catheter mount 200a such as those for the conduit port 250c, the interface port 300c, the design of the reverse connectors 280c and 330c as shown in FIGS. 4A-4B, and the design of the valves 380c as shown in FIGS. 5A-5B.

With reference to FIG. 9, the suction port 250c of the switch catheter mount 200c can be comprised of a suction port 350c directly opposite the interface port 300c and the switch 390c directly opposite the conduit port 250c. The suction port 350c can have an opening 360c configured to permit insertion of a suction catheter 160 into the mount body 210c and into the flow channel 212c. In the illustrated embodiment, the suction port 350c and opening 360c have a generally circular shape formed about the interface axis 204c. Furthermore, circumscribing the opening 360c is an engagement lip 362c configured to be received within a locking slot 520 of the valve 380c being used. In some embodiments, the size and shape of the port 350c and the opening 360c may vary. For example, ports and openings may also be elliptical, such as an oval, or polygonal, such as a square, rectangle, pentagon, hexagon or the like.

The switch 390c can be configured to redirect the suction catheter depending upon the positioning of the switch 390c. As such, the switch 390c generally could be constructed of a material that would not substantially deform when contacting the suction catheter 160. Such materials could include, but are not limited to, plastics such as ABS, polycarbonate, polypropylene, HTPE, metals, composites, polymers, or other suitable materials. In the illustrated embodiment, the switch 390c has a top portion 392c and a rod-shaped redirection portion 394c that is configured to redirect the suction catheter 160. Because the redirection portion 394c is configured to redirect the suction catheter 160, in some embodiments, the redirection portion 394c generally has a large cross-sectional area to facilitate contact with a suction catheter 160 that has been inserted into the mount body 210c. If the cross-sectional area is not sufficiently wide in a direction perpendicular to the cross-sectional plane shown in FIG. 9, a user of the device may find it difficult to redirect a suction catheter 160 into the conduit port 250c. In some embodiments, the redirection portion 394c may have at least a portion with a rectangular cross-sectional area. In some embodiments, the redirection portion could encompass other elliptical shapes, such as ovals and polygonal shapes, such as pentagons, hexagons, and the like. In some configurations, the redirection portion 394c is sufficiently wide to increase the likelihood of contact with the catheter while also enabling flow through the flow path within the catheter mount. As such, the redirection portion 394c preferably does not totally obstruct the flow path. In some applications, the redirection portion 394c can extend the full width of the flow path but, because it is positioned inline with the inlet flow passage, the redirection portion will not fully occlude the flow. In some embodiments, the redirection portion 394c will only extend a portion of each of the flow paths.

In addition, in some embodiments such as that in FIGS. 8A and 8B, the switch may also have a biasing mechanism 396c, such as a spring, which forces the switch 390c into an "interface access" position when no forces are placed on the switch 390c. In some embodiments, a locking mechanism may be added to maintain the switch in the desired position. In some embodiments, the switch can remain in the desired position solely due to friction between the mount body 210c and the redirection portion 394c.

In operation, when the switch 394c is not depressed and remains in an "interface access" position, a suction catheter 160 inserted into the mount body 210c is not impeded and is capable of accessing the interior of the interface port 300c and possibly any attached tubing. When the switch 394c is depressed and in the "conduit access" position, a suction catheter 160 inserted into the mount body 210c is impeded from entering the interface port 300c of the mount body. As such, the suction catheter can be redirected into the conduit port 250c where it is capable of accessing the interior of the conduit port 250c and possibly any attached tubing. Therefore, placement of the opening 360c and use of the switch 390c advantageously allows direct access to both tubes without removing the catheter mount 200c from the system. This reduces the amount of time necessary in maintaining the interior surfaces of a respiratory assistance system since the catheter mount 200c need not be removed from the system in order to perform this routine maintenance.

In a preferred embodiment, the intersection of the conduit axis 202a and the interface axis 204a form an intersection angle $I_c$. In some embodiments of the switch catheter mount 200c, the intersection angle $I_c$ could be any angle from about 30° to about 150°. In some embodiments, the intersection angle $I_c$ ranges from about 45° to about 135°. In some embodiments, the intersection angle Ic ranges from about 80° to about 110°. Finally, in some embodiments, such as that illustrated in FIGS. 8 and 9, the intersection angle $I_c$ is about 90°. The intersection angle $I_c$ used for a particular embodiment of the switch catheter mount 200c can be based on other design parameters such as, but not limited to, the offset angle $O_c$, the offset distance $H_c$, the length of the redirection portion 394c, and the projection distance $P_c$ of the switch 390c.

In addition to the other parameters, such as the offset distance $H_c$, the offset distance $D_a$, and the offset angle $O_a$, discussed above with respect to the angled catheter mount 200a, additional design parameters include the length of the redirection portion 394c. In some embodiments, the length of the redirection portion can be between about 0.5 cm and about 3.0 cm. In some embodiments, the length of the redirection portion can be between about 0.5 cm and about 2.0 cm. In some embodiments, the length of the redirection portion can be between about 0.5 cm and about 1.0 cm. Finally, in some embodiments, the length of the redirection portion is about 1.0 cm.

Furthermore, another parameter that can also be configured is the projection distance $P_c$ defined as the distance between the conduit axis 250c and a parallel line tangential to the part of the redirection portion closest to the suction port 350c. In some embodiments, the projection distance $P_c$ can be between about 0.1 cm and about 1.0 cm. In some embodiments, the projection distance $P_c$ can be between about 0.3 cm and about 0.8 cm. In some embodiments, the projection distance $P_c$ can be between about 0.4 cm and about 0.6 cm. Finally, in some embodiments, the projection distance $P_c$ is about 0.5 cm.

Wide-Range Valve Catheter Mount

FIGS. 10-12 are illustrations of an embodiment of a wide-range valve catheter mount 200d that is configured to allow a suction catheter 160 to access both ports and possibly the corresponding tubes attached thereto due to the wide-range valve 600. The wide-range valve catheter mount 200d comprises a conduit port 250d, an interface port 300d, and a suction port 350d. The catheter mount 200d has a mount body 210d configured to allow fluid communication between the conduit port 250d, the interface port 300d, and the suction port 350d. The construction of the catheter mount 200d is similar to the preceding catheter mounts 200a, 200b, 200c with the main exception being that the wide-range valve catheter mount 200d uses a larger, wide-range valve 600 rather than the smaller valve 380 of the other catheter mounts. As such, reference should be made to the description of the angled catheter mount 200a for a description of the components contained in the wide-range valve catheter mount 200d such as those for the conduit port 250d, the interface port 300d, and the design of the reverse connectors 280d and 330d as shown in FIGS. 4A-4B.

Figure 10A:
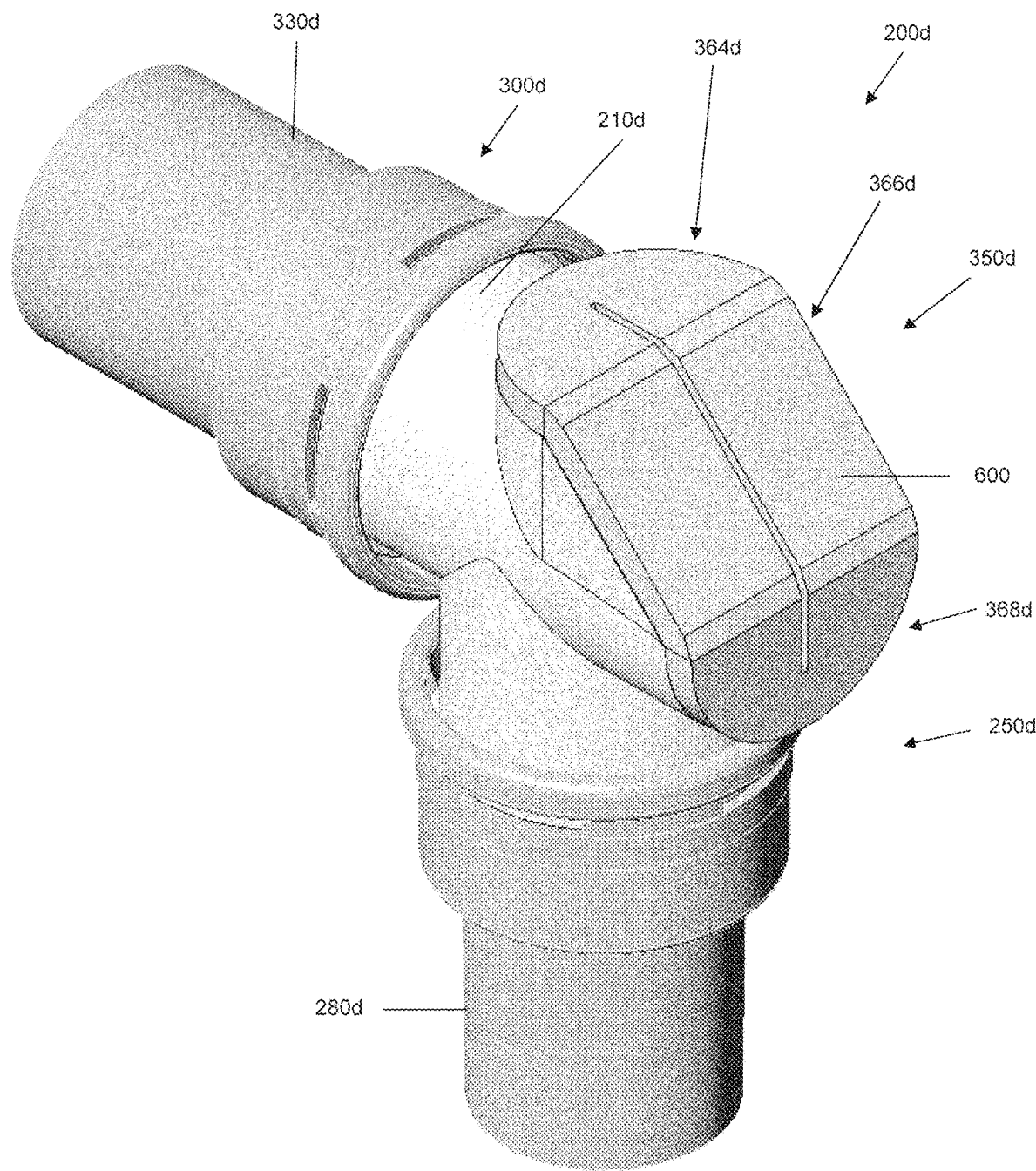
FIG. 10A is a perspective view of a catheter mount that is arranged and configured in accordance with certain features, aspects and advantages of the present invention.
Figure 10B:
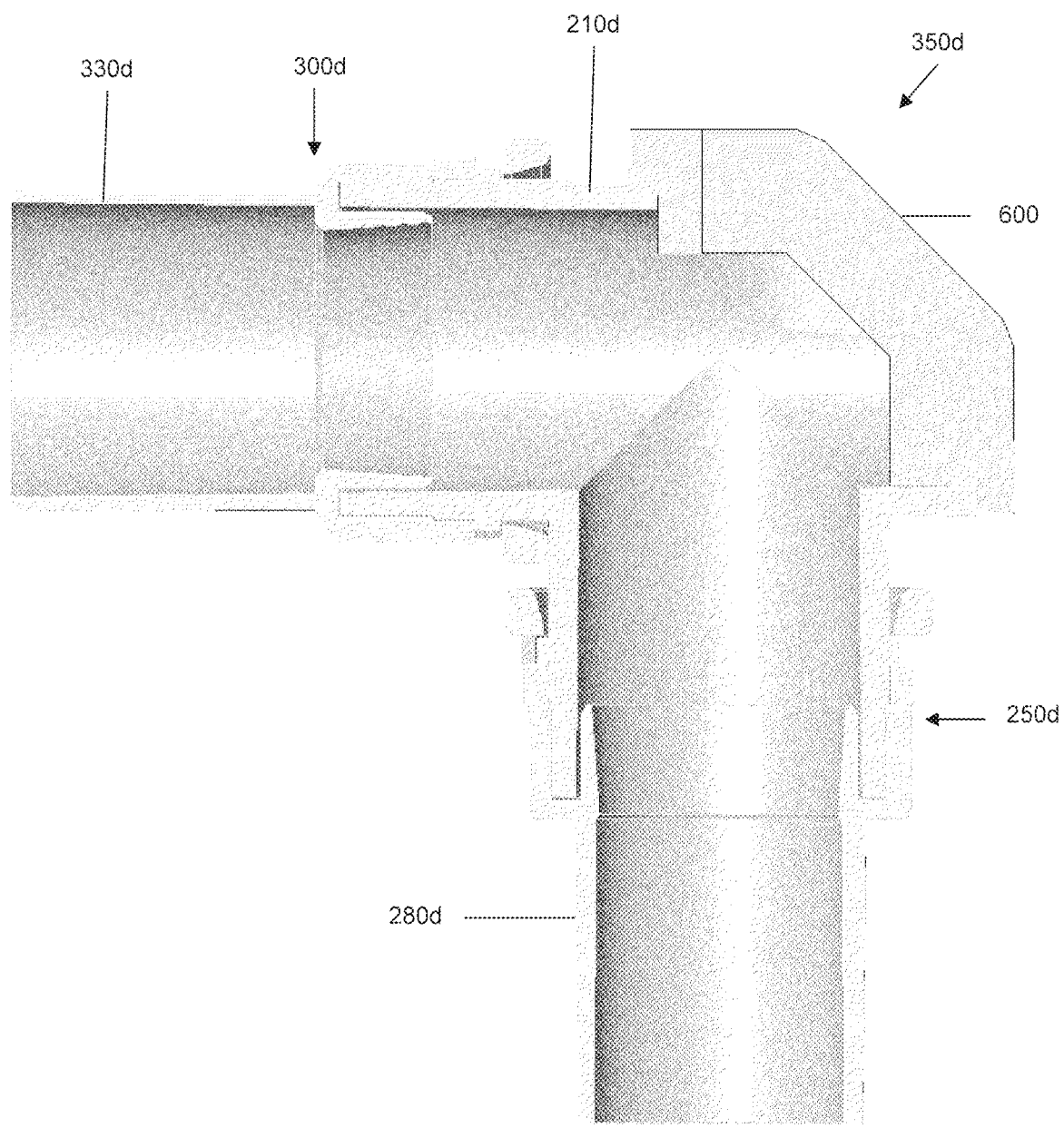
FIG. 10B is a section view of the catheter mount of FIG. 10A.

In the embodiment illustrated in FIGS. 10A and 10B, the suction port 350d of the wide range catheter mount 200d is comprised of a flat top surface 364d having a semi-circular shape, a flat chamfered surface 366d with a rectangular shape, a flat trailing surface 368d with a semicircular shape. Other configurations are possible.

Figure 11A:
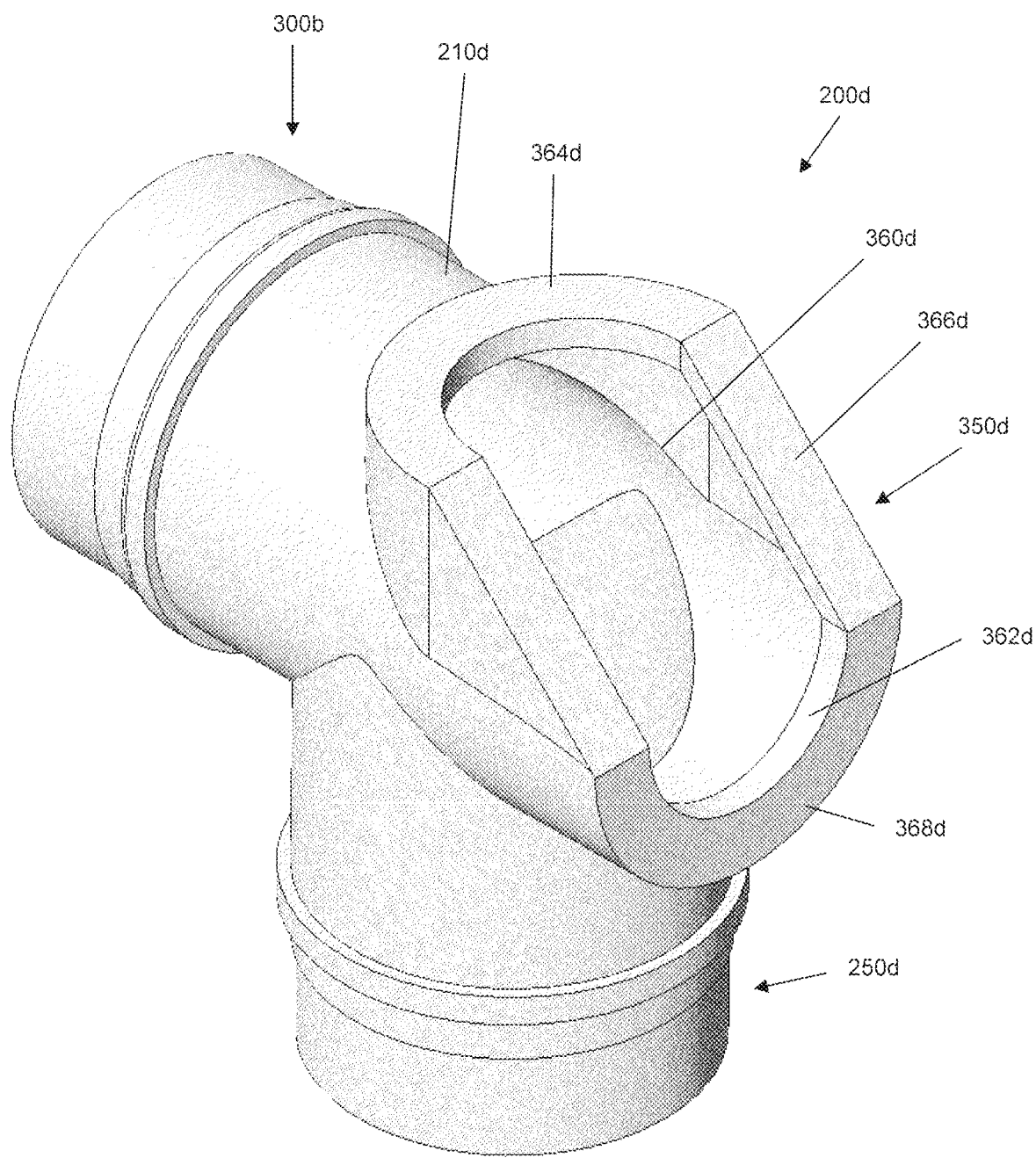
FIG. 11A is a perspective view of a portion of the catheter mount of FIG. 10A.
Figure 11B:
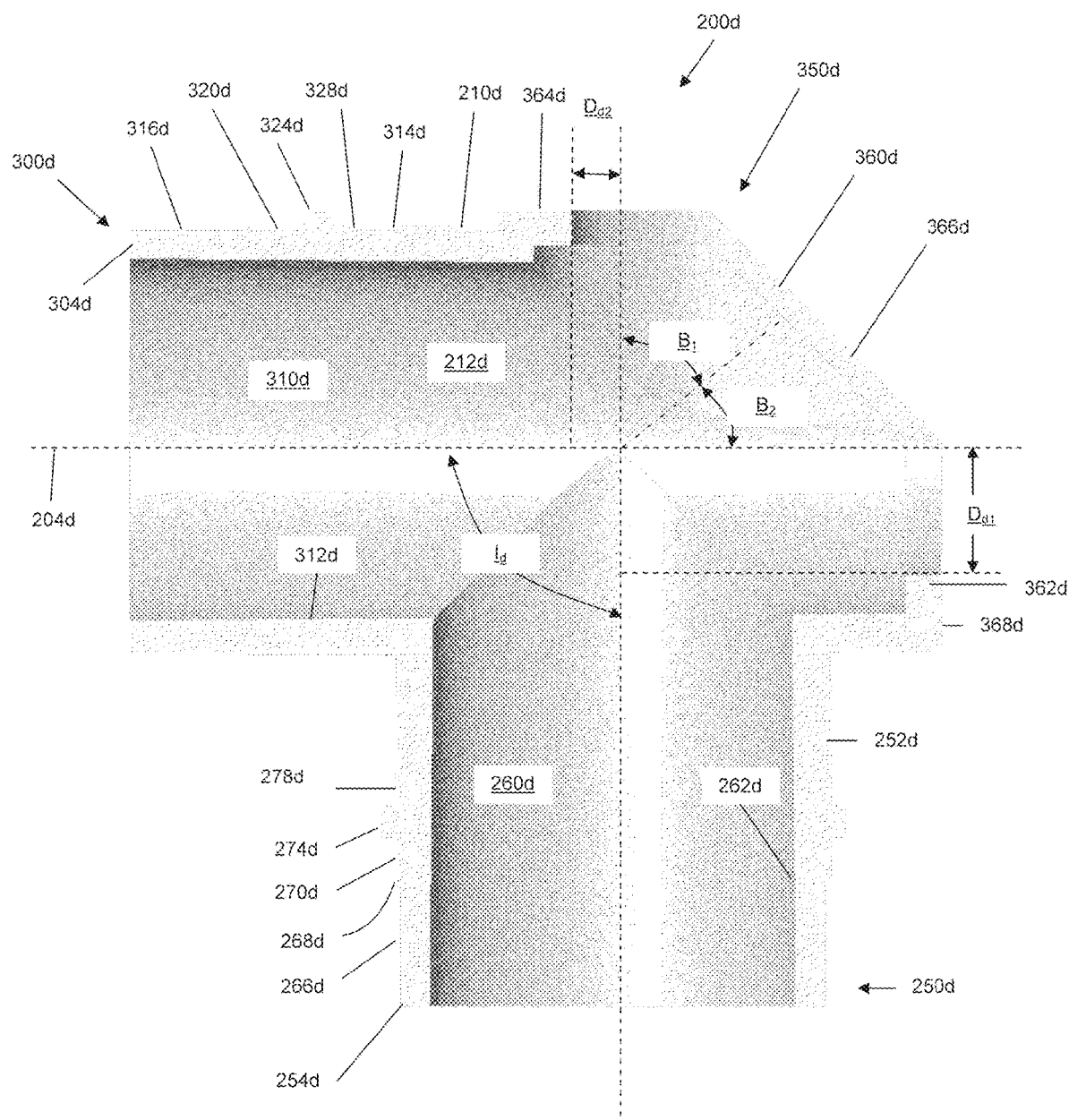
FIG. 11B is a section view of the portion of the catheter mount of FIG. 11A.

With reference to FIGS. 11A and 11B, an opening 360d can be defined through one or more of the surfaces 364d, 366d, 368d. In the illustrated embodiment, the shape of the opening 360d can vary along the surfaces 364d, 366d, 368d. Along both the top and trailing surfaces 364d, 368d, the opening 360d can have a generally semicircular shape and, along the chamfered surface 366d, the opening 360d can have a generally rectangular shape.

In the illustrated embodiment, the area of the opening 360d is approximately 1.2 times greater than the area of the conduit port 250c or the interface port 300d. In some embodiments, the area of the opening 360d can be greater than or less than the area of the ports 250c, 300c.

The opening 360*d* can be centered on these surfaces such that an engagement lip 362*d* is formed and defined by the shape of the opening 360*d*. The engagement lip 362*d* can be configured to be received within an annular locking slot 640 of the wide-range valve 600.

Figure 10C:
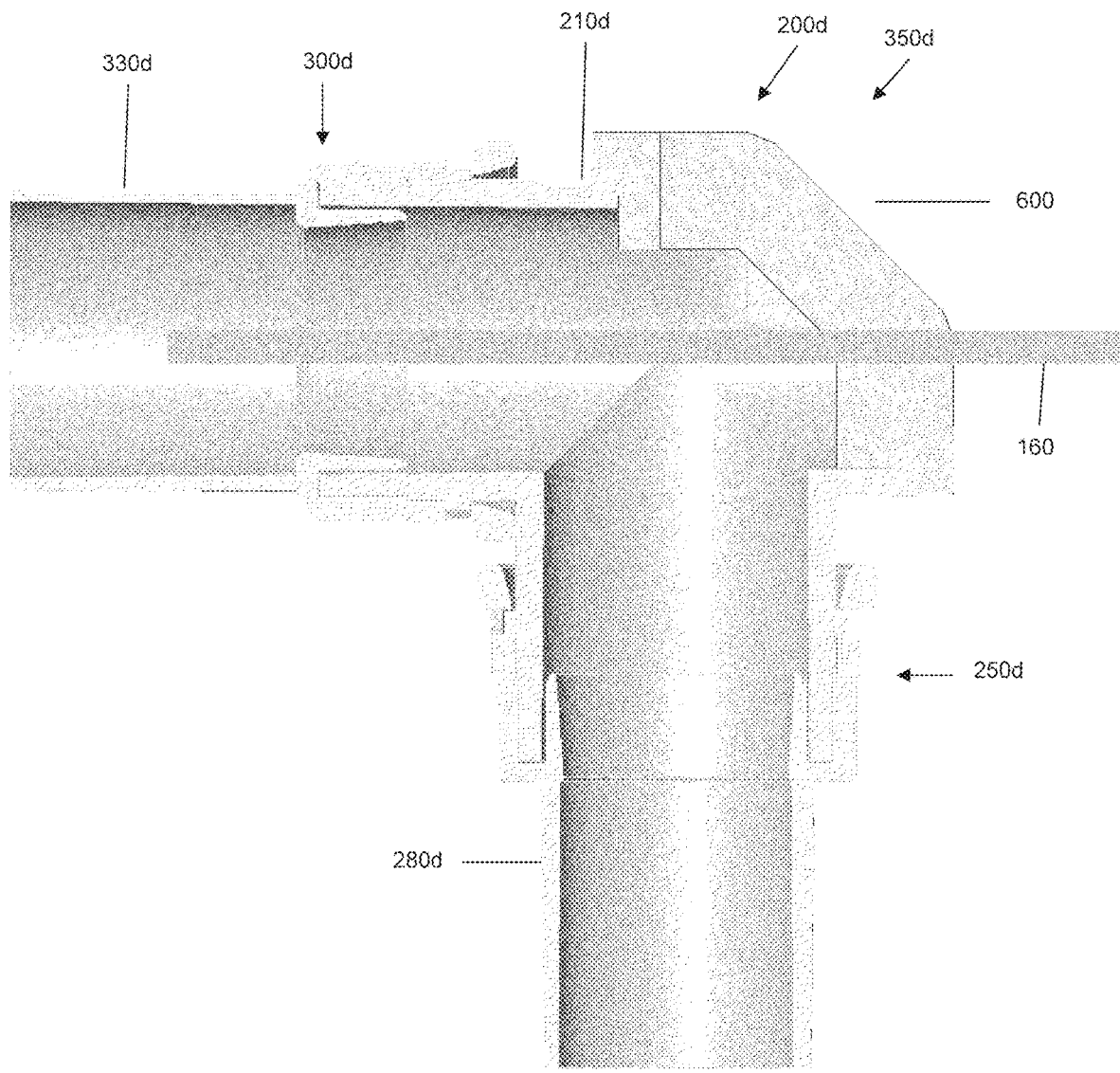
FIG. 10C is a section view of the catheter mount of FIG. 10A showing a schematic suction tube inserted into a first portion of the catheter mount.
Figure 10D:
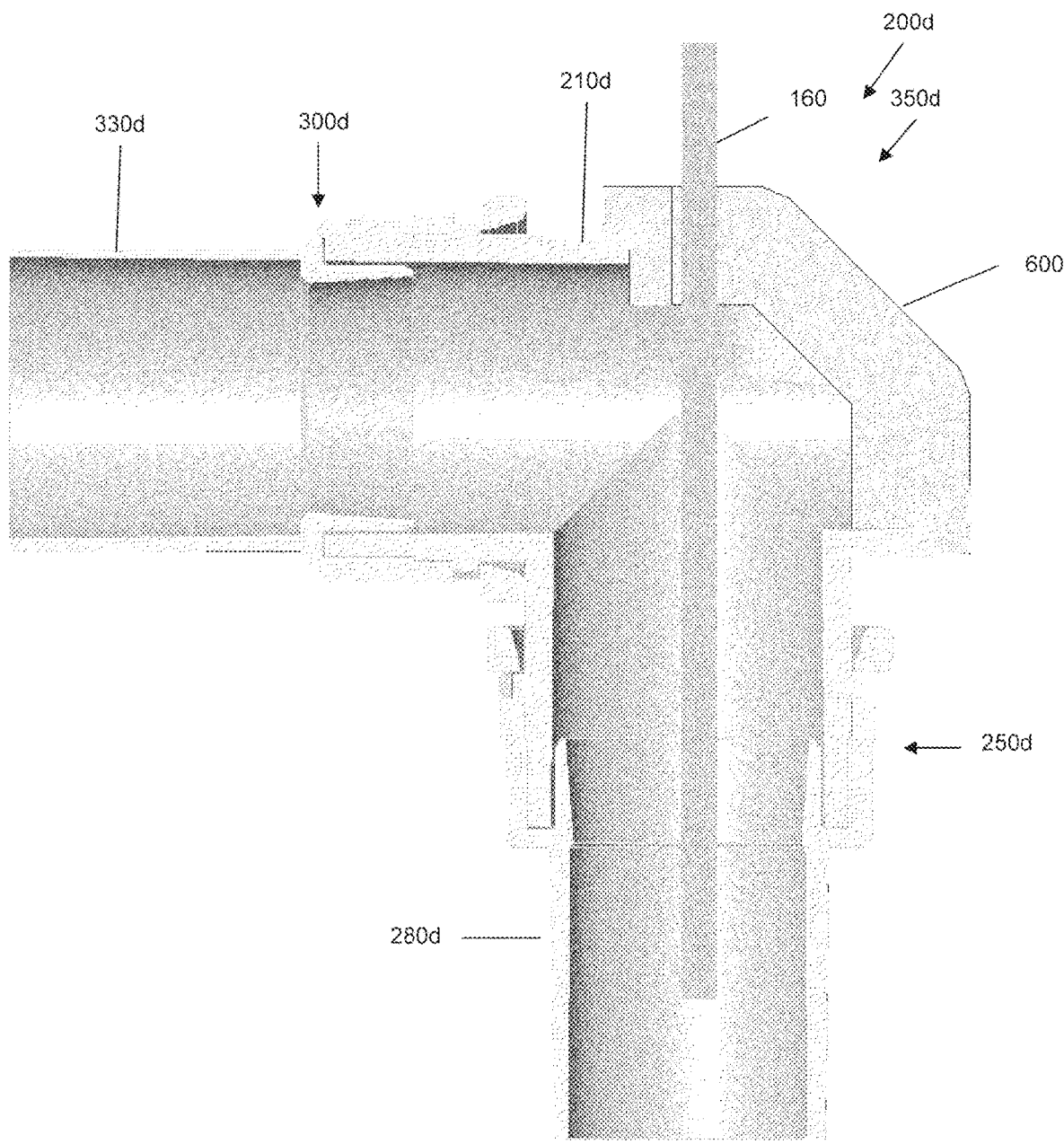
FIG. 10D is a section view of the catheter mount of FIG. 10A showing a schematic suction tube inserted into a second portion of the catheter mount.

With reference to FIGS. 10C and 10D, the location and configuration of the opening 360*d* allows the suction catheter 160 to access both, as illustrated in FIG. 10C, the interior of the conduit port 250*d* and possibly any attached tubing and, as illustrated in FIG. 10D, the interior of the interface port 300*d* and possibly any attached tubing. Accordingly, the illustrated configuration advantageously allows direct access to both tubes without having to remove the catheter mount 200*d* from the system. This reduces the amount of time spent in maintaining the interior surfaces of a respiratory assistance system because the catheter mount 200*d* facilitates this routine maintenance without requiring removal.

In some embodiments, the intersection of the conduit axis 202*d* and the interface axis 204*d* form an intersection angle $I_d$. In some embodiments of the wide-range valve catheter mount 200*d*, the intersection angle $I_d$ could range from about 60° to about 120°. In some embodiments, the intersection angle $I_d$ ranges from about 70° to about 110°. In some embodiments, the intersection angle $I_d$ ranges from about 80° to about 100°. In some embodiments, such as that illustrated in FIGS. 10-12, the intersection angle $I_d$ is about 90°. The intersection angle $I_d$ used for a particular embodiment of the wide-range catheter mount 200*d* can be based on other design parameters such as, but not limited to, the size and placement of the opening 360*d* and the wide-range valve 600.

In order to allow access to both the conduit port 250*d* and the interface port 300*d*, the opening 360*d* can be of sufficient size such that both the conduit axis 202*d* and the interface axis 204*d* pass through the aperture 360*d* along the top surface 364*d* and the trailing surface 368*d* respectively. Furthermore, to facilitate the use of a suction catheter 160 with this embodiment of the wide-range catheter mount 360*d*, the chamfered surface 366*d* is angled such that: (1) the first intermediate angle $B_1$, defined as the angle of intersection between the conduit axis 202*a* and a line both coplanar with the conduit axis 202*a* and perpendicular to the chamfered surface 366*d*, is approximately equal to 45° and (2) the second intermediate angle $B_2$, defined as the angle of intersection between the interface axis 204*a* and a line both coplanar with the interface axis 202*a* and perpendicular to the chamfered surface 366*d*, is approximately equal to 45°. As such, in the illustrated embodiment, both intermediate angles are generally equal. In other embodiments, the intermediate angles may differ. In some embodiments, such as those where the intersection angle $I_d$ is not equal to 90°, the angles may differ. In general, the angles can be determined using the equation $I_d = B_1 + B_2$.

Other embodiments of the wide-range valve catheter mount 200*d* may have openings 360*d* of different sizes, shapes and placements. In some embodiments, the chamfered surface 366*d* may be omitted such that the two surfaces, 364*d* and 368*d*, are directly connected. In some embodiments, the top surface 364*d* and the trailing surfaces 368*d* may be omitted such that only the chamfered surface 366*d* exists. The placement of the opening 360*d* may also be changed such that the opening 360*d* along the top and trailing surfaces 364*d* and 368*d* is placed further back such that the opening is not intersected by one or more of the axis 202*d* and axis 204*d*. In yet other embodiments, the opening 360*d* may be moved forward such that the opening 360*d* along the chamfered surface 366*d* is intersected by either of the axes 202*d*, 204*d* or both.

Figure 12A:
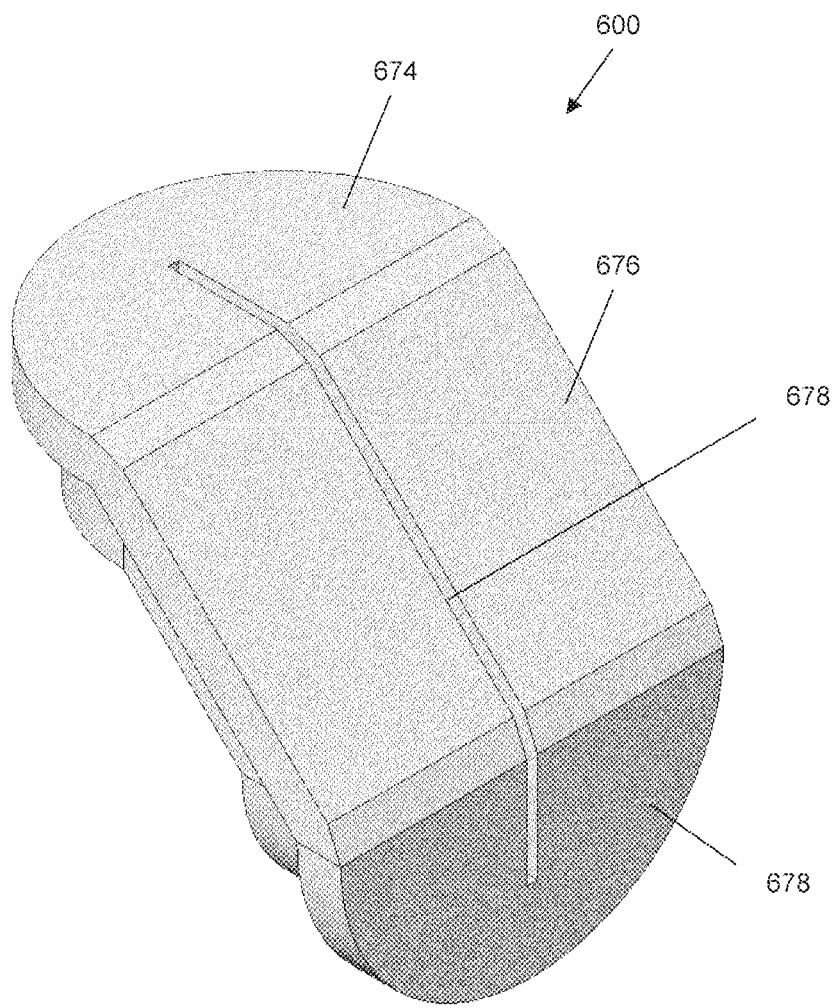
FIG. 12A is a perspective view of a portion of the catheter mount of FIG. 10A.
Figure 12B:
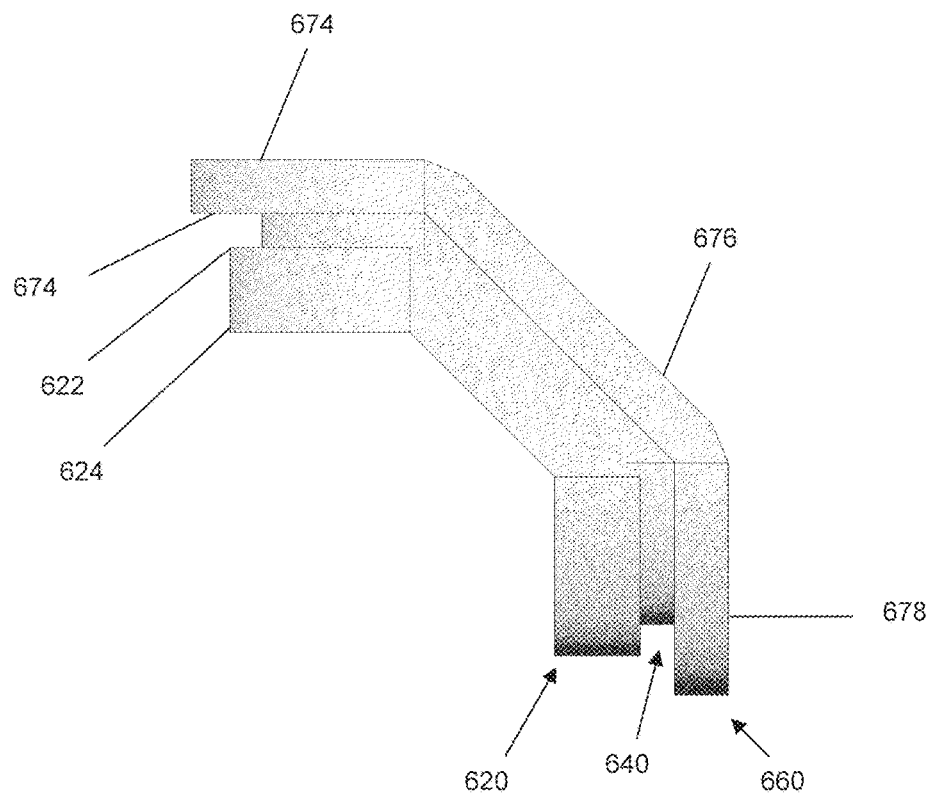
FIG. 12B is a side view of the portion of the catheter mount of FIG. 12A.
Figure 12C:
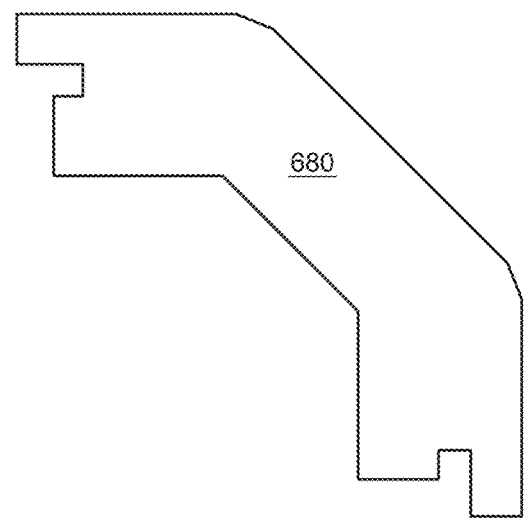
FIG. 12C is a section view of the portion of the catheter mount of FIG. 12A.

In order to provide a generally hermetic seal when a suction catheter 160 is not being used and a reduced flow through the port when the suction catheter 160 is being used, a wide-range valve 600 can be used in conjunction with the wide-range valve catheter mount 200*d* and received within the opening 360*d* of the suction port 350*d*. FIGS. 12A-12C are illustrations of an embodiment of the wide-range valve 600 which can be used to provide a generally hermetic seal. The valve 600 can be manufactured from any suitable materials keeping in mind the desire to allow the valve to accommodate the suction catheter 160. Preferably, the valve 600 is manufactured from materials with sufficient elasticity such that the valve 600 can deform and conform to the shape of the opening 360*d* to provide a more effective seal.

With reference to FIG. 12B, the wide-range valve 600 has an insertion member 620, a locking slot 640, an end cap 660, and inner channel 680. The insertion member 620 is configured to be received within the mount body 210*d* when fully assembled. The shape of the insertion member 620 generally corresponds to the shape of the opening 360*d* being used for the wide-range catheter mount 200*d*. In a preferred embodiment, the insertion member 620 is sized such that, at least at the trailing end 622, the insertion member 900 has dimensions greater than those of the opening 360*d*. In the illustrated embodiment, the shape of the insertion member 620 remains generally constant throughout its length from the leading edge 624 to the trailing edge 622. In other embodiments, in order to facilitate insertion of the insertion portion 620 into the aperture 360*d* due to the differences in size, the insertion portion 320 can be tapered along the leading end 624. In some embodiments, the size and shape of the leading end 624 is equal to, or slightly smaller than, the size and shape of the opening 360*d* in order to facilitate insertion into the catheter mount 200*d*.

The locking slot 640 can be configured to reduce or eliminate the likelihood of movement of the wide-range valve 600 when attached to the mount body 210*d*. The dimensions of the annular locking slot 640 generally correspond to the dimensions of the engagement lip 362*d*. The annular locking slot 640 can be sized and shaped to be slightly larger than the opening 360*d* in order to provide a more generally hermetic seal. The size and shape can be slightly greater depending on the elastic properties of the wide-range valve 600. When fully inserted, the sections of the wide-range valve 600 in contact with the mount body 210*d* surfaces are compressed and form a more advantageous seal. In some embodiments, the dimensions chosen are based on the type of material being used, the amount of sealing required, and considerations of difficulty of insertion and removal of the valve.

The end cap 660 is configured to control fluid communication to the inner channel 680. At the leading end 662 end cap 660 is comprised of a flat surface 664 configured to abut the top surface 364*d*, the chamfered surface 366*d*, and the trailing surface 368*d*, of the mount body 210*d* when the valve 600 is fully inserted within the mount body 210*d*. The size and shape of the end cap 660 generally corresponds to the size and shape of surfaces 364*d*, 366*d*, 368*d*. The end cap 660 has slit 670 running through the end cap 660 and into the inner channel 680. In the illustrated embodiment, a single slit 670 runs through a central section of the top portion 674, an entire central section of the chamfered portion 676, and a central section of the trailing portion 678 of the valve. The slit 670 allow a suction catheter 160 to be inserted into the valve 600 and into the inner channel 680 without removal of the valve 600. When a suction catheter 160 is removed from the slit 670, the slit can return to its original shape and provide a generally hermetic seal. In some embodiments, the slit runs solely through the chamfered portion 676. In some embodiments, multiple slits may be used. In one non-limiting example, a first slit can exist along a central part of the top portion 674 and a second slit can exist along a central part of the trailing portion 678.

Ball-Joint Catheter Mount

Figure 13:
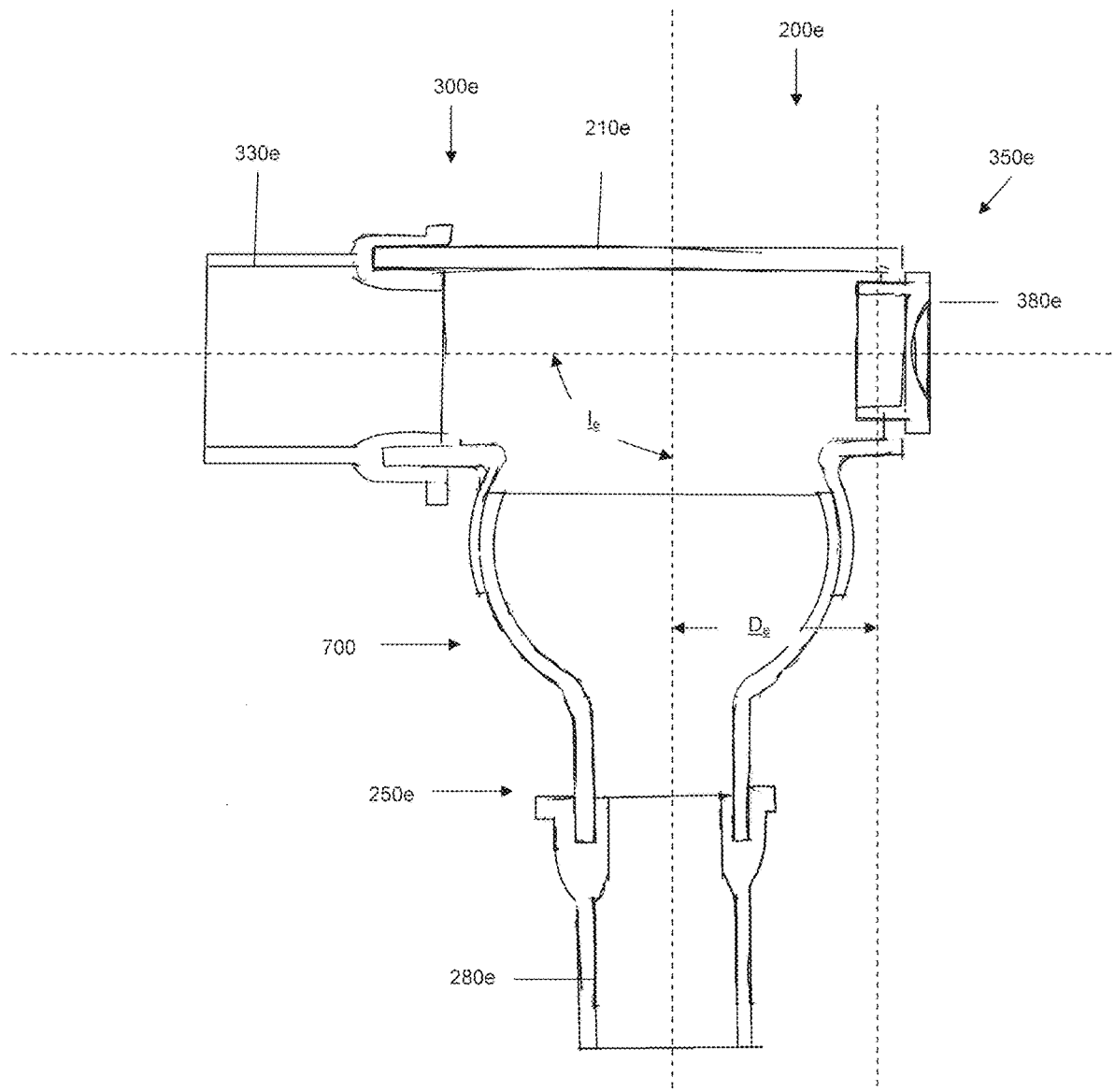
FIG. 13 is a section view of another catheter mount that is arranged and configured in accordance with certain features, aspects and advantages of the present invention.

FIG. 13 illustrates an embodiment of a ball-joint catheter mount 200e with a conduit port 250e and an interface port 300e. The conduit portion 250e and the interface port 300e can rotate relative to each other to allow a suction catheter 160 to access to both connectors and possibly the corresponding tubes attached thereto. In the embodiment shown, the ball-joint catheter mount 200e also has a suction port 350e opposite the interface port 300e. The ball-joint catheter mount 200e has a mount body 210e configured to allow fluid communication between the conduit port 250e, the interface port 300e, and the suction port 350e through an interior flow channel 212e. Additionally, the conduit port 250e is attached to a ball-joint assembly 700 allowing the conduit port 250e to be rotated. In some embodiments, the suction port 350a is oriented opposite the conduit port 250a with the interface port 300e attached to the ball-joint assembly 700. The construction of the ball-joint catheter mount 200e is similar to that of the above-described catheter mounts such as the angled catheter mount 200a with the main exception that, rather than being fixed, the ball-joint catheter mount 200e can be rotated thereby changing the interface axis 204e and resulting in a modifiable intersection angle $I_e$. As such, reference should be made to the description of the dual-valve catheter mount 200b for a description of the components contained in the switch catheter mount 200a such as those for the conduit port 250c, the interface port 300c, the design of the reverse connectors 280c and 330c as shown in FIGS. 4A-4B, and the design of the valves 380c as shown in FIGS. 5A-5B.

During normal operation, ball-joint catheter mount 200e can have an intersection angle $I_e$ of 90° or greater to facilitate placement near the interface 150. When necessary, the ball-joint catheter mount can be rotated at the ball joint assembly 700 to decrease the intersection angle $I_e$ and, similar to the angled catheter mount 200a, allow a suction catheter 160 to access both the conduit port 250e and the interface port 300e. In some configurations, the ball-joint assembly includes an arcuate inner surface such that the catheter can be better directed toward the conduit port 250e. In the illustrated configuration, the suction port 350e is non-movably positioned relative to an axis of the interface port 300e while being movably positioned relative to an axis of the conduit port 250e.

In some configurations, a connector (e.g., an intermediate suction tube connector) can be provided with a port and valve assembly. In such configurations, the port and valve assembly can be angled to provide each of access to one or more components between the flow generators (e.g., ventilator) and the catheter mount. In such configurations, it is possible to use the connector in combination with a standard catheter mount.

All features of the embodiments described above can be combined and integrated. Thus, as one non-limiting example, a dual-valve catheter mount 200b may also have a narrow intersection angle $I_b$ akin to the angled catheter mount 200a. As another non-limiting example, the ball-joint catheter mount 200e can also have a wide-range valve 600 of the wide-range valve catheter mount 200d rather than the smaller valve 380e. The remaining combinations and permutations are also included herein as embodiments.

Although the present invention has been described in terms of a certain embodiment, other embodiments apparent to those of ordinary skill in the art also are within the scope of this invention. Thus, various changes and modifications may be made without departing from the spirit and scope of the invention. For instance, various components may be repositioned as desired. Moreover, not all of the features, aspects and advantages are necessarily required to practice the present invention. Accordingly, the scope of the present invention is intended to be defined only by the claims that follow.

What is claimed is:

1. A system comprising a catheter mount configured to be attached to a respiratory apparatus, the catheter mount comprising:
    a plurality of ports in fluid communication with each other, wherein the plurality of ports comprise:
        an interface port configured to connect to an interface tube;
        a conduit port configured to connect to a conduit tube; and
        a suction port configured to allow insertion of a suction catheter; and
    a valve configured to allow direct access to both the conduit tube and interface tube through the suction port.

2. The system of claim 1, wherein the valve comprises a flat chamfered surface surrounding an access slit formed in the valve.

3. The system of claim 1, wherein the valve comprises a flat top surface and/or a flat trailing surface.

4. The system of claim 1, wherein the valve comprises at least one of a rectangular flat chamfered surface, a substantially semi-circular flat top surface, and a substantially semi-circular flat trailing surface.

5. The system of claim 1, wherein the valve is deformable.

6. The system of claim 1, further comprising a breathing circuit comprising an inspiratory tube and an expiratory tube.

7. A system comprising a catheter mount configured to be attached to a respiratory apparatus, the catheter mount comprising:
    a plurality of ports in fluid communication with each other, wherein the plurality of ports comprise:
        an interface port configured to connect to an interface tube;
        a conduit port configured to connect to a conduit tube; and
        a suction port configured to allow insertion of a suction catheter; and
    a valve associated with the suction port, wherein the interface port comprises an interface axis and the conduit port comprises a conduit axis, wherein the interface axis and the conduit axis intersect the valve.

8. The system of claim 7, wherein an intersection angle is defined between the conduit axis and interface axis, wherein the intersection angle is between about 60 degrees and about 120 degrees.

9. The system of claim 8, wherein the intersection angle is about 90 degrees.

10. The system of claim 7, wherein a first intermediate angle defined as the angle of intersection between the conduit axis and a line perpendicular to a chamfered surface of the valve is approximately equal to 45 degrees.

11. The system of claim 10, wherein a second intermediate angle defined as the angle of intersection between the interface axis and a line perpendicular to a chamfered surface of the valve is approximately equal to 45 degrees.

12. The system of claim 7, wherein the suction port comprises a suction port opening, wherein the valve comprises a slit, wherein the opening of the suction port and/or the slit of the valve overlaps with the interface axis and the conduit axis.

13. The system of claim 7, further comprising a breathing circuit comprising an inspiratory tube and an expiratory tube.

14. A system comprising a catheter mount configured to be attached to a respiratory apparatus, the catheter mount comprising:
   a plurality of ports in fluid communication with each other, wherein the plurality of ports comprise:
      an interface port configured to connect to an interface tube;
      a conduit port configured to connect to a conduit tube; and
      a suction port configured to allow insertion of a suction catheter; and
   a valve, wherein the interface port comprises an interface axis and the conduit port comprises a conduit axis, wherein the valve is associated with the suction port and is configured to allow the suction catheter to be inserted through the valve and selectively extend along the interface axis or the conduit axis.

15. The system of claim 14, wherein the valve comprises at least one slit.

16. The system of claim 14, wherein the valve comprises a slit, the slit being configured to enable the suction catheter to be inserted through the slit to access the interface port and the conduit port, the slit being configured to return to an original shape when the suction catheter is removed from the slit.

17. The system of claim 14, wherein the valve comprises an annular locking slot, wherein the suction port comprises an engagement lip configured to be received within the annular locking slot of the valve.

18. The system of claim 17, wherein the suction port comprises an opening, the annular locking slot being sized and shaped slightly larger than the opening.

19. The system of claim 14, wherein the valve is configured to provide a substantially hermetic seal.

20. The system of claim 14, further comprising a breathing circuit comprising an inspiratory tube and an expiratory tube.

* * * * *